(12) United States Patent
Leonard et al.

(10) Patent No.: US 8,221,739 B2
(45) Date of Patent: Jul. 17, 2012

(54) METHOD OF CANCER TREATMENT

(75) Inventors: Arnold S. Leonard, Minneapolis, MN (US); Daniel A. Saltzman, Mendota Heights, MN (US); Mark J. Mueller, Spooner, WI (US)

(73) Assignee: Botanic Oil Innovations, Inc., Spooner, WI (US)

( * ) Notice: Subject to any disclaimer, the term of this patent is extended or adjusted under 35 U.S.C. 154(b) by 0 days.

(21) Appl. No.: 12/425,927

(22) Filed: Apr. 17, 2009

(65) Prior Publication Data

US 2010/0098665 A1 Apr. 22, 2010

Related U.S. Application Data

(63) Continuation-in-part of application No. 10/834,587, filed on Apr. 29, 2004, now abandoned.

(51) Int. Cl.
*A61K 48/00* (2006.01)
*A01K 63/00* (2006.01)
(52) U.S. Cl. .................................. 424/93.2; 424/93.48
(58) Field of Classification Search .................. 424/93.2, 424/93.48
See application file for complete search history.

(56) References Cited

U.S. PATENT DOCUMENTS

| 6,685,935 | B1 | 2/2004 | Pawelek et al. |
| 7,588,767 | B2 | 9/2009 | Szalay et al. |
| 8,066,987 | B2 | 11/2011 | Moore et al. |
| 2005/0244375 | A1 | 11/2005 | Leonard et al. |
| 2006/0105423 | A1 | 5/2006 | Rapp et al. |
| 2007/0128301 | A1 | 6/2007 | Saltzman et al. |
| 2007/0243310 | A1 | 10/2007 | Leonard et al. |
| 2008/0107758 | A1 | 5/2008 | Crutchfield |

FOREIGN PATENT DOCUMENTS

| EP | 833660 A1 | 4/1998 |
| EP | 833660 A4 | 4/2003 |
| EP | 833660 B1 | 12/2006 |
| EP | 2028270 A2 | 2/2009 |
| WO | WO 00/32211 | 6/2000 |
| WO | WO-0124637 A1 | 4/2001 |
| WO | WO-0226819 A2 | 4/2002 |
| WO | WO-03063593 A1 | 8/2003 |
| WO | WO-03072789 A2 | 9/2003 |
| WO | WO 2005/116233 A | 12/2005 |
| WO | WO-2007025333 A1 | 3/2007 |
| WO | WO-2007039192 A2 | 4/2007 |

OTHER PUBLICATIONS

Eckenberg et al (Cytokine, 9(7): 488-498, 1997).*
(Kimchi-Sarfaty et al., 2007, Science, pp. 525-528.*
B.S. Sorenson, K.L. Banton, N.L. Frykman, A. S. Leonard, D.A. Saltzman; Attenuated *Salmonella typhimurium* with [L-2 Gene Reduces Pulmonary Metastases in Murine Osteosarcoma; Symposium: Selected Papers presented at the 2007 Meeting of the Musculoskeletal Tumor Society; Association of Bone and Joint Surgeons; 2008.
B. S. Sorenson, K. L. Banton, N.L. Frykman, A.S. Leonard, D.A. Saltzman; Attenuated *Salmonella typhimurium* with interleukin 2 gene prevents the establishment of pulmonary metastases in a model of osteosarcoma; Department of Surgery, Division of Pediatric Surgery, University of Minnesota Medical School, Minneapolis, MN 55455, USA; Feb. 7, 2008.
D.A. Saltzman, C.P. Heise, D.E. Hasz, M. Zebede, S. M. Kelly, R. Curtiss III, A. S. Leonard, P.M. Anderson; Attenuated *Salmonella typhimurium* Containing Interleukin-2 Decreases MC-38 Hepatic Metastases: A Novel Anti-tumor Agent; Cancer Biotherapy & Radiopharmaceuticals; vol. 11, No. 2, 1996; pp. 145-153.
L.J. Soto III, B.S. Sorenson, B.W. Nelson, S.J. Solis, A.S. Leonard, D.A. Saltzman; Preferential Proliferation of Attenuated *Salmonella typhimurium* Within Neuroblastoma; Journal of Pediatric Surgery, vol. 39, No. 6, 2004; pp. 937-940.
D.A. Saltzman, E. Katsanis, C.P. Heise, D.E. Hasz, S.M. Kelly, R. Curtiss III, A.S. Leonard, P.M. Anderson; Patterns of Hepatic and Splenic Colonization by an Attenuated Strain of *Salmonelly typhimurium* Containing the gene for human interleukin-2: a novel anti-tumor agent; Cancer Biotherapy & Radiopharmaceuticals; vol. 12, No. 1, 1997; pp. 37-45.
D.A. Saltzman, E. Katsanis, C.P. Heise, D.E. Hasz, V. Vigdorovich, S.M. Kelly, R. Curtiss III, A.S. Leonard, P.M. Anderson; Antitumor Mechanisms of Attenuated *Salmonella typhimurium* Cotaining the Gene for Human Interleukin-2: A Novel Antitumor Agent?; Journal of Pediatric Surgery, vol. 32, No. 2, 1997; pp. 301-306.
B.A. Feltis, D.A. Sahar, A.S. Kim, D.A. Saltzman, A.S. Leonard, T.D. Sielaff; Cyclooxygenase-2 Inhibition Augments the Hepatic Antitumor Effect of Oral *Salmonella Typhimurium* in a Model of Mouse Metastatic Colon Cancer; American Society of Colon and Rectal Surgeons Annual Meeting, San Diego, CA, Jun. 2-7, 2001; 6 pgs.
B.A. Feltis, J.S. Miller, D.A. Sahar, A.S. Kim, D.A. Saltzman, A.S. Leonard, C.L. Wells, T.D. Sielaff; Liver and Circulating NK1.1 CD3 Cells Are Increased in Infection with Attenuated *Salmonella typhimurium* and Are Associated with Reduced Tumor in Murine Liver Cancer; Journal of Surgical Research 107, 101-107 (2002).
D.A. Saltzman; Cancer immunotherapy based on the killin gof *Salmonella typhimurium*-infected tumour cells; Expert Opin. Biol. Ther. (2005) 5(4):443-449. Parker et al., "Fatty Acid Composition and Oxidative Stability of Cold-pressed Edible Seed Oils", Journal of Food Science 68:4: 1240-1243, 2003.
Ustun, G. et al.; Investigation of technological properties of *Nigella sativa* (Black Cumin) seed oil; JAOCS 67(12)958; 1990.
Parry, J. et al.; Fatty acid content and antioxidant properties of cold-pressed black raspberry seed oil and meal; Journal of Food Science 69(3)189; 2004.
Atta, M.B.; Some characteristics of nigella (*Nigella sativa* L.) seed cultivated in Egypt and its lipid profile; Food Chemistry 83:63; 2003.
European Application Serial No. 09171109.3, Extended European Search Report mailed Aug. 12, 2010, 8 pgs.
Soto, L. J, et al., "Attenuated *Salmonella typhimurium* prevents the establishment of unresectable hepatic metastases and improves survival in a murine model.", J Pediatr Surg., 38(7), (Jul. 2003), p. 1075-1079.

(Continued)

*Primary Examiner* — Thaian N Ton
*Assistant Examiner* — Magdalene Sgagias
(74) *Attorney, Agent, or Firm* — Schwegman, Lundberg & Woessner, P.A.

(57) ABSTRACT

A method and composition for treating cancer comprising administering to a patient an effective amount of attenuated *Salmonella typhimurium* containing a plasmid carrying the coding sequence encoding a truncated human interleukin-2 and optionally an oil containing a high antioxidant concentration.

1 Claim, 22 Drawing Sheets

OTHER PUBLICATIONS

Soto, L. J, et al., "Attenuated *Salmonella typhimurium*-Induced Immunity to Hepatic Colorectal Metastases", Abstract #P79, Proceedings of the Society of Surgical Oncology 57th Annual Cancer Symposium, (2004), p. S107.

"European Application Serial No. 09171109.3, Extended European Search Report Response Filed Apr. 19, 2011", 7.

Curtiss, R., et al., "*Salmonella typhimurium* deletion mutants lacking adenylate cyclase and cyclic AMP receptor protein are avirulent and immunogenic", Infect Immun., 55(12), (Dec. 1987), 3035-43.

Galan, J. E, et al., "Cloning and characterization of the asd gene of *Salmonella typhimurium*: use in stable maintenance of recombinant plasmids in *Salmonella* vaccine strains", Gene, 94(1), (Sep. 28, 1990), 29-35.

Schodel, F., et al., "Hybrid hepatitis B virus core-pre-S proteins synthesized in avirulent *Salmonella typhimurium* and *Salmonella typhi* for oral vaccination", Infect Immun., 62(5), (May 1994), 1669-76.

Sorenson, B. et al.: "Safety and immunogenicity of *Salmonella typhimurium* expressing C-terminal truncated human IL-2 in a murine model"; Biologics: Targets and Therapy vol. 4, 2009; pp. 61-73.

Nelson, B.W.: "Antioxidant oil augments cytotoxic immune response to attenuated *Salmonella typhimurium*"; Department of Surgery, University; XP-002460183, Apr. 30, 2003.

Barnett, S.J. et al.: "Attenuated *Salmonella typhimurium* invades and decreases tumor burden in neuroblastoma"; Journal of Pediatric Surgery, vol. 40, No. 6; Jun. 1, 2005; pp. 993-998.

R.W. Owen et al., "The antioxidant/anticancer potential of phenolic compounds isolated from olive oil", European Journal of Cancer 36 (2000) 1235-1247.

Verma, Inder M. et al., "Gene Therapy: Twenty First Century Medicine", Ann. Rev. Biochem 2005 74:711-738.

Wada, Leslie et al., "Amendment Activity and Phenolic Content of Oregon Caneberries", Journal of Agricultural and Food Chemistry, 50:3495-3500, Jun. 5, 2002.

\* cited by examiner

1
Met-Try-Arg-Met-Gln-Leu-Leu-Ser-Cys-Ile-Ala-Leu-Ser-Leu-Ala-Leu-Val-Thr-Asn-
20
Ser-

Ala-Pro-Thr-Ser-Ser-Ser-Thr-Lys-Lys-Thr-Gln-Leu-Gln-Leu-Glu-His-Leu-Leu-Leu-
40                                  50

Asp-Leu-Gln-Met-Ile-Leu-Asn-Gly-Ile-Asn-Asn-Tyr-Lys-Asn-Pro-Lys-Leu-Thr-Arg-
60                                  70

Met-Leu-Thr-Phe-Lys-Phe-Tyr-Met-Pro-Lys-Lys-Ala-Thr-Glu-Leu-Lys-His-Leu-Gln-
80                                  90

Cys-Leu-Glu-Glu-Glu-Leu-Lys-Pro-Leu-Glu-Glu-Val-Leu-Asn-Leu-Ala-Gln-Ser-Lys-
100                                 110

Asn-Phe-His-Leu-Arg-Pro-Arg-Asp-Leu-Ile-Ser-Asn-Ile-Asn-Val-Ile-Val-Leu-Glu-Leu-
120                                 130

Lys-Gly-Ser-Glu-Thr-Thr-Phe-Met-Cys-Glu-Tyr-Ala-Asp-Glu-Thr-Ala-Thr-Ile-Val-
140                          150      153

Glu-Phe-Leu-Asn-Arg-Trp-Ile-Thr-Phe-Cys-Gln-Ser-Ile-Ile-Ser-Thr-Leu-Thr

Fig. 2

```
atgtacaggatgcaactcctgtcttgcattgcactaagtcttgcacttgtcacaaacagt
gcacctacttcaagttctacaaagaaaacagctacaactggagcatttactgctggat
ttacagatgattttgaatggaattaataattacaagaatcccaaactcaccaggatgctc
acatttaagttttacatgcccaagaaggccacagaactgaaacatctttcagtgtctagaa
gaagaactcaaacctctggaggaagtgctaaatttagctcaaagcaaaaactttcactta
agacccagggacttaatcagcaatatcaacgtaatagttctggaactaaagggatctgaa
acaacattcatgtgtgaatatgctgatgagacagcaaccattgtagaatttctgaacaga
tggattacctttgtcaaagcatcatctcaatactgacttga
```

Fig. 3 p<0.01
Control, SalpIL2
Control, SalpIL2 + Oil
Oil, SalpIL2
Oil, SalpIL2 + Oil p<0.05
Oil, SalpIL2
Oil, SalpIL2 + Oil p<0.05
No significance p<0.01
Control, SalpIL2
Control, SalpIL2 + Oil
Oil, SalpIL2
Oil, SalpIL2 + Oil

*Fig. 17: Treatment of Neuroblastoma with SalpIL2*

Fig. 18: Treatment of Neuroblastoma with SalpIL2

*Fig. 19: Treatment of Neuroblastoma with SalpIL2*

*Fig. 20: Treatment of Pulmonary Metastases from Osteosarcoma: tumor number.*

SEQUENCE LISTING

```
<160> NUMBER OF SEQ ID NOS: 7

<210> SEQ ID NO 1
<211> LENGTH: 276
<212> TYPE: DNA
<213> ORGANISM: Homo sapiens
<220> FEATURE:
<221> NAME/KEY: terminator
<222> LOCATION: (274)..(276)

<400> SEQUENCE: 1
atggctccta ctagctcgag cactaagaaa actcaactgc aattggagca tctgctgctg      60
gatctgcaga tgattctgaa tggcatcaat aactacaaga accctaagct gactcgcatg     120
ctgactttca aattctacat gccgaaaaag gctaccgagc tcaaacatct ccagtgcctg     180
gaagaggaac tgaagccgct ggaggaagta cttaacctgg cacagtctaa gaacttccac     240
ctgcgtccgc gtgacctgat ctccaacatc aagtaa                              276

<210> SEQ ID NO 2
<211> LENGTH: 91
<212> TYPE: PRT
<213> ORGANISM: Homo sapiens

<400> SEQUENCE: 2

Met Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
            20                  25                  30

Lys Asn Pro Lys Leu Thr Arg Met Leu Thr Phe Lys Phe Tyr Met Pro
```

```
                  35                  40                  45
Lys Lys Ala Thr Glu Leu Lys His Leu Gln Cys Leu Glu Glu Glu Leu
 50                  55                  60

Lys Pro Leu Glu Glu Val Leu Asn Leu Ala Gln Ser Lys Asn Phe His
 65                  70                  75                  80

Leu Arg Pro Arg Asp Leu Ile Ser Asn Ile Lys
                 85                  90

<210> SEQ ID NO 3
<211> LENGTH: 153
<212> TYPE: PRT
<213> ORGANISM: Homo sapiens

<400> SEQUENCE: 3

Met Tyr Arg Met Gln Leu Leu Ser Cys Ile Ala Leu Ser Leu Ala Leu
 1               5                  10                  15

Val Thr Asn Ser Ala Pro Thr Ser Ser Ser Thr Lys Lys Thr Gln Leu
                20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
 50                  55                  60

Tyr Met Pro Lys Lys Ala Thr Glu Leu Lys His Leu Gln Cys Leu Glu
 65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 4
<211> LENGTH: 462
<212> TYPE: DNA
<213> ORGANISM: Homo sapiens

<400> SEQUENCE: 4
atgtacagga tgcaactcct gtcttgcatt gcactaagtc ttgcacttgt cacaaacagt      60
gcacctactt caagttctac aaagaaaaca cagctacaac tggagcattt actgctggat    120
ttacagatga ttttgaatgg aattaataat tacaagaatc ccaaactcac caggatgctc    180
acatttaagt tttacatgcc caagaaggcc acagaactga acatcttca gtgtctagaa     240 gaagaactca aacctctgga ggaagtgcta aatttagctc aaagcaaaaa ctttcactta    300
agacccaggg acttaatcag caatatcaac gtaatagttc tggaactaaa gggatctgaa    360
acaacattca tgtgtgaata tgctgatgag acagcaacca ttgtagaatt tctgaacaga    420
tggattacct tttgtcaaag catcatctca acactgactt ga                       462

<210> SEQ ID NO 5
<211> LENGTH: 404
<212> TYPE: DNA
<213> ORGANISM: Homo sapiens

<400> SEQUENCE: 5
```

```
atggctccta ctagctcgag cactaagaaa actcaactgc aattggagca tctgctgctg      60
gatctgcaga tgattctgaa tggcatcaat aactacaaga accctaagct gactcgcatg     120
ctgactttca aattctacat gccgaaaaag gctaccgagc tcaaacatct ccagtgcctg     180
gaagaggaac tgaagccgct ggaggaagta cttaacctgg cacagtctaa gaacttccac     240
ctgcgtccgc gtgacctgat ctccaacatc aagtaatcgt tcttgagctg aagggatccg     300
aaaccacctt catgtgcgaa tacgctgacg aaaccgccac cattgtggag ttcctgaacc     360
gttggatcac cttttgccaa tcgatcatta gcacgttaac ttaa                      404
```

```
<210> SEQ ID NO 6
<211> LENGTH: 405
<212> TYPE: DNA
<213> ORGANISM: Homo sapiens

<400> SEQUENCE: 6
atggctccta ctagctcgag cactaagaaa actcaactgc aattggagca tctgctgctg      60
gatctgcaga tgattctgaa tggcatcaat aactacaaga accctaagct gactcgcatg     120
ctgactttca aattctacat gccgaaaaag gctaccgagc tcaaacatct ccagtgcctg     180
gaagaggaac tgaagccgct ggaggaagta cttaacctgg cacagtctaa gaacttccac     240
ctgcgtccgc gtgacctgat ctccaacatc aatgtaatcg ttcttgagct gaagggatcc     300
gaaaccacct tcatgtgcga atacgctgac gaaaccgcca ccattgtgga gttcctgaac     360
cgttggatca ccttttgcca atcgatcatt agcacgttaa cttaa                     405
```

```
<210> SEQ ID NO 7
<211> LENGTH: 134
<212> TYPE: PRT
<213> ORGANISM: Homo sapiens

<400> SEQUENCE: 7

Met Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
            20                  25                  30

Lys Asn Pro Lys Leu Thr Arg Met Leu Thr Phe Lys Phe Tyr Met Pro
        35                  40                  45

Lys Lys Ala Thr Glu Leu Lys His Leu Gln Cys Leu Glu Glu Glu Leu
    50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Cys Gln Ser
        115                 120                 125

Ile Ile Ser Thr Leu Thr
        130
```

METHOD OF CANCER TREATMENT

CROSS-REFERENCE TO RELATED APPLICATION

The present application is a continuation in part of and claims priority of U.S. patent application Ser. No. 10/834,587, filed Apr. 29, 2004 now abandoned, the content of which is hereby incorporated by reference in its entirety.

REFERENCE TO SEQUENCE LISTING

A sequence listing on a compact disc is submitted with the present application. The material on the compact disc is hereby incorporated by reference in its entirety.

BACKGROUND OF THE INVENTION

It is estimated that 150,000 new cases of colorectal cancer occur in North America every year. Of these patients, it is expected that 40 to 50 percent will experience a recurrence within five years. Furthermore, it is known that the 75 to 80 percent of patients with a recurrence have the liver as one of the involved sites for metastasis. Unresectable metastatic carcinoma of the liver continues to have a very poor prognosis despite recent advances with chemotherapeutic and radiotherapeutic strategies, radiofrequency ablation and cryotherapy. It is true that when caught at an early stage, Duke's stages A or B (i.e., malignant invasion confined to the intestinal wall), a multimodal approach of both surgery and chemotherapy have proven to be beneficial. However, when colorectal cancer metastasizes, it usually does so in the liver and if the metastases are unresectable there is currently no effective treatment strategy with a reasonable hope of a cure.

BRIEF DESCRIPTION OF THE DRAWINGS

FIG. 2 shows the DNA sequence (SEQ ID NO:4) of a DNA encoding normal human interleukin-2.

FIG. 3 shows the amino acid sequence (SEQ ID NO:3) of the normal human interleukin-2 protein encoded by SEQ ID NO:4.

SUMMARY OF THE INVENTION

Figure 1:
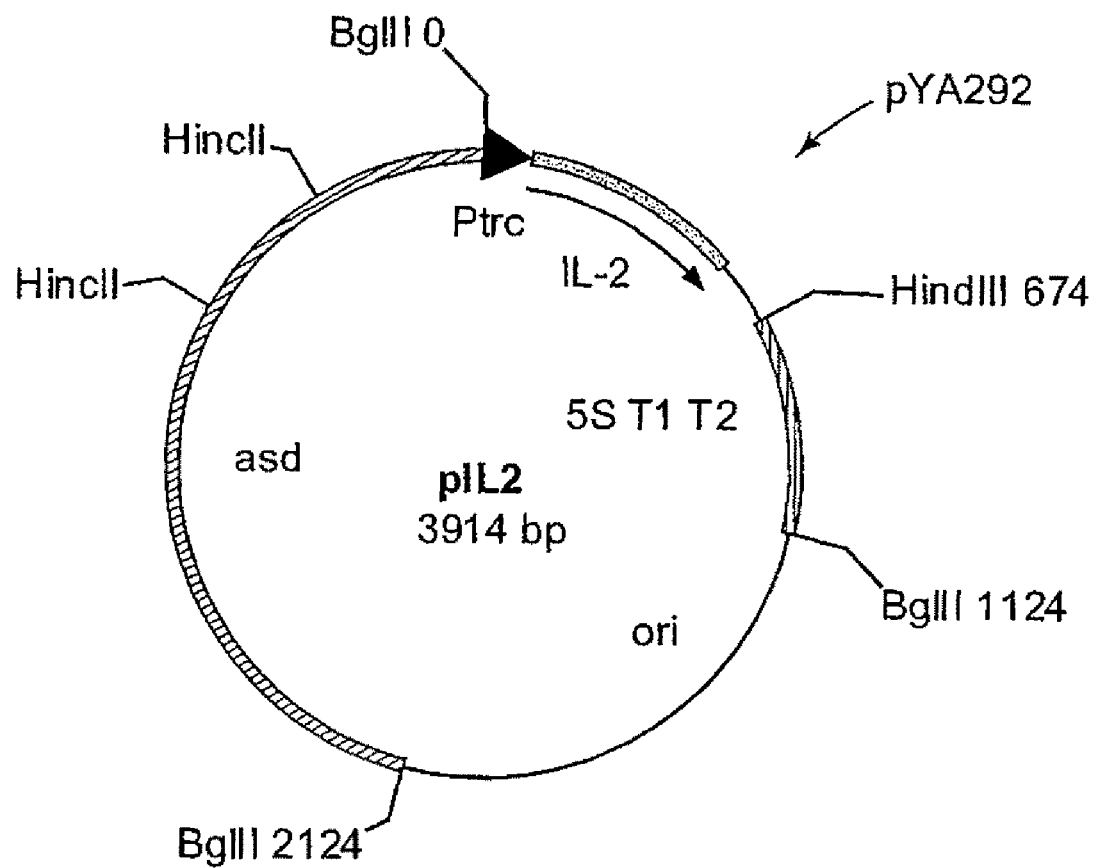
FIG. 1 shows the pIL2 plasmid containing the coding sequence encoding the human interleukin-2 protein inserted into *Salmonella typhimurium* χ4550pIL2.

The present invention provides a method for treating cancer. The method includes administering to a patient a composition comprising an effective amount of attenuated *Salmonella typhimurium* containing a plasmid carrying a coding sequence encoding for a truncated human interleukin-2. An oil containing a high antioxidant concentration selected from the group consisting of black raspberry oil, red raspberry oil, blackberry oil, marionberry oil, boysenberry oil, evergreen blackberry oil and black cumin oil is also optionally administered as part of the method.

The present invention further provides the plasmid carrying the coding sequence encoding for truncated human interleukin-2 is pYA292.

The present invention also provides the attenuated *Salmonella typhimurium* containing the coding sequence encoding for the truncated human interleukin-2 lacks the cyclic AMP and cAMP receptor protein.

The present invention further provides the attenuated *Salmonella typhimurium* lacking the enzyme aspartate semialdehyde dehydrogenase and the pYA292 plasmid containing the enzyme aspartate semialdehyde dehydrogenase, which renders the attenuated *Salmonella typhimurium* harmless and simultaneously expresses the gene for human IL-2.

The present invention also provides the oil containing a high antioxidant concentration being extracted by using a high pressure press and maintaining the temperature of the oil below one hundred twenty degrees Fahrenheit.

The present invention further provides a method wherein the coding sequence encoding truncated human interleukin-2 has an eighty percent identity to SEQ ID NO:. 1

The present invention also provides a method wherein the coding sequence encoding truncated human interleukin-2 has an eighty five percent identity to SEQ ID NO:. 1

The present invention further provides a method wherein the coding sequence encoding truncated human interleukin-2 has a ninety percent identity to SEQ ID NO: 1.

The present invention further provides a method wherein the coding sequence encoding truncated human interleukin-2 has a ninety five percent identity to SEQ ID NO: 1.

The present invention further provides a method wherein a dose containing approximately $10^6$ to $10^8$ of the attenuated *Salmonella typhimurium* containing a plasmid carrying the coding sequence encoding the truncated human interleukin-2 is administered once during treatment and a dose of approximately a half teaspoon of an oil containing a high antioxidant concentration selected from the group consisting of black raspberry oil, red raspberry oil, blackberry oil, marionberry oil, boysenberry oil, evergreen blackberry oil and black cumin oil is optionally administered twice a day.

The present invention further provides a method of reducing murine hepatic metastases by oral treatment with attenuated *Salmonella typhimurium* containing a plasmid carrying the coding sequence encoding the truncated human interleukin-2.

The present invention further provides a method of reducing the volume and mass of retroperitoneal neuroblastoma tumors in mice by oral treatment with attenuated *Salmonella typhimurium* containing a plasmid carrying the coding sequence encoding the truncated human interleukin-2.

The present invention further provides a method of reducing the number and volume of pulmonary metastases in mice injected with osteosarcoma cells and then given an oral treatment with attenuated *Salmonella typhimurium* containing a plasmid carrying the coding sequence encoding the truncated human interleukin-2.

DETAILED DESCRIPTION

Definitions

"Attenuated" means bacteria selected or altered to greatly diminish its capacity to cause disease, but still able to retain its ability to colonize the gut associated lymphoid tissue.

"CD4+" and "CD4+ cell" mean a helper subset of T cells.

"CD8+" and "CD8+ cell" mean a cytotoxic subset of T cells.

"Coding sequence" and "coding region" are used interchangeably and refer to a polynucleotide that encodes a protein and, when placed under the control of appropriate regulatory sequences, expresses the encoded protein. The boundaries of a coding region are generally determined by a translation start codon at its 5' end and a translation stop codon at its 3' end.

"Gated Lymphocytes" refers to lymphocytes that have been analyzed in a fluorescent cell sorter.

"IL-2" means the protein human interleukin-2.

"NK" or "NK cell" means natural killer cell.

"Oil" refers to highly potent antioxidant oils.

"Operably linked" refers to a juxtaposition wherein the components so described are in a relationship permitting them to function in their intended manner. A regulator sequence is operably linked to a coding region when it is joined in such a way that expression of the coding region is achieved under conditions compatible with the regulatory sequence.

"Regulatory Sequence" refers to a nucleotide sequence that regulates expression of a coding region to which it is operably linked. Nonlimiting examples of regulatory sequences include promoters, transcription initiation sites, translation start sites, translation stop sites and terminators.

Human Interleukin-2

Interleukin-2 (IL-2) (SEQ ID NO: 3, FIG. 3) is a protein naturally produced by the human body which promotes lymphocyte proliferation and enhances the cytolytic function of T cells and natural killer (NK) cells. It is thus able to stimulate the immune system to produce cancer-destroying white blood cells. IL-2 based immunotherapy in certain types of cancer has been studied for years with limited success.

Attenuated *Salmonella typhimurium*

While IL-2 is naturally produced by the human body, its maximum effectiveness requires a higher concentration and more specific delivery vector to the disease site. However, high doses of IL-2 are found to result in severe toxicity in many patients. A solution to this problem was found in using a live bacterial strain of *Salmonella typhimurium* which was attenuated to greatly diminish its capacity to cause disease. *S. typhimurium* is used due to its natural ability to colonize the gut associated lymphoid tissue (GALT), liver and spleen.

Colonization of the liver by the attenuated *S. typhimurium* further initiates a generalized cellular response against the bacteria or can persist as a carrier state. The χ4550 strain of *S. typhimurium* used in the present invention contains a gene deletion constructed by transposon mutagenesis with Tn10 followed by selection for furasic acid resistance. This method of genetic alteration leads to deletional loss of Tn10 and adjacent DNA sequences to produce a deletion of aspartate semialdehyde dehydrogenase (asd). This mutation imposes a requirement for diaminopimelic acid. The lack of the asd enzyme in these bacteria leads to the inability to construct a stable cell wall causing lethal lysis of the *S. typhimurium*. Thus, to insure stable expression of a desired protein, a plasmid-(pYA292) was constructed which carries the asd gene. In order to insure avirulence of the *S. typhimurium* strain, standard P22 phage transduction of the mouse virulent *S. typhimurium* SR-11 strain χ3306 was employed to construct the χ4550 strain that lacks the ability to synthesize adenylate cyclase and the cAMP receptor protein (CRP). Cyclic AMP and cAMP receptor protein are necessary for the transcription of many genes and operons concerned with the transport and breakdown of catabolites. Although cAMP is found in mammalian tissue and theoretically could be used by the bacteria to increase the potential for virulence, the lack of a cAMP receptor protein should abolish any benefit that could occur by the uptake of cAMP by these mutant bacteria.

A synthetic cDNA (SEQ ID NO: 5), coding for a truncated human IL-2 protein, optimized for expression in *Escherichia coli* was inserted into plasmid pYA292 using well known methods. The truncated cDNA (SEQ ID NO:1) is a part of the synthetic IL-2 nucleotide sequence (SEQ ID NO: 5). This sequence is one nucleotide short of the sequence that was intended to code for a full-length mature human IL-2 protein. By "mature" is meant a protein lacking the beginning (N-terminal) 20 amino acid signal sequence that is cleaved off as the molecule is secreted from the a human cell. The mutation that occurred is a deletion of a "t" nucleotide between the "a" at position 272 and the "g" at position 273. This resulted in an in-frame taa stop codon at position 274 that truncated the resultant IL-2 protein. The resulting DNA nucleotide sequence is SEQ ID NO: 1 and the expressed protein is SEQ ID NO: 2. Both the aspartate semialdehyde dehydrogenase (asd+) vector and the synthetic truncated human IL-2 cDNA were digested to completion with restriction enzymes EcoRI (Promega, Madison, Wis.) and Hind III (New England Biolabs, Beverly, Mass.). The ~3.4 kb linearized vector fragment of pYA292 and the EcoRI-HindIII fragment of the IL-2 gene were isolated following agarose gel electrophoresis using the PrepaGene Kit (BioRad, Hercules, Calif.). The IL-2 gene fragment was ligated into the pYA292 vector using T4 DNA ligase (Promega, Madison, Wis.) with a 3:1 molar excess of insert and incubating for 4 hours at 16° C. The ligation mix was then electroporated into the χ4550 strain of attenuated *S. typhimurium. S. typhimurium*, Δcya-1 Δcrp-1 ΔasdA1 strain χ4550, was grown in Luria Broth (Sigma, St. Louis, Mo.) containing 50 mg/ml diaminopimelic acid (DAP). Cultures were grown to an absorbance of 0.200 at $OD_{600}$ (approximately $10^8$ colony forming units (CFU)/ml broth) and the cells were prepared for electroporation. Plasmid vector pYA292 and the ligation mix were electroporated into χ4550 utilizing an electroporation device (BioRad) with 0.2 cm disposable cuvettes. Cells were pulsed at 2.5 kV and 25 μF with a pulse controller at 200 ohms. Cells were then subsequently plated on Luria agar without DAP and recombinant clones were identified using the Magic Mini-Prep DNA Purification System (Promega), and restriction enzyme digestion with EcoRI and HindIII and gel electrophoresis with 1.2 agarose. The restriction enzyme mapping revealed a plasmid corresponding to that expected for an insert of the IL-2 fragment in pYA292 and the plasmid was renamed pIL2. The new transformant was renamed χ4550(pIL2). Transforming an asd deleted strain with the plasmid (pIL2) allows for the stable expression of IL-2.

As discussed above, stability of this vector is maintained because the particular strain of *S. typhimurium* used here (χ4550) lacks the enzyme aspartate semialdehyde dehydrogenase (asd), which, conversely, the plasmid containing the IL-2 gene (pIL2) contains. Bacteria lacking asd cannot make diaminopimelic acid (DAP), an essential component of the bacterial cell wall and, thus, would not long survive. Thus, if the attenuated *S. typhimurium* were to attempt to revert to its wild-type strain and lose the plasmid, it would die a "DAP-less" death. Because the loss of the IL-2 containing plasmid would also result in the loss of the plasmid encoded asd, stable expression of the IL-2 gene is achieved.

It is believed that a coding sequence encoding truncated human interleukin-2 having an eighty percent identity to SEQ ID NO: 1 would be effective in the treating and preventing cancerous tumors. It is further believed that a coding sequence encoding truncated human interleukin-2 having an eighty five percent identity to SEQ ID NO: 1 would be effective in treating and preventing cancerous tumors. It is also believed that a coding sequence encoding truncated human interleukin-2 having a ninety percent identity to SEQ ID NO: 1 would be effective in treating and preventing cancerous tumors. It is further believed that a coding sequence encoding truncated human interleukin-2 having a ninety five percent identity to SEQ ID NO: 1 would be effective in treating and preventing cancerous tumors.

High Antioxidant Plant Oils

Natural oils derived from plant materials are produced through a method of cold pressing the raw plant material. In a preferred embodiment waste products of black raspberries, *Rubus occidentalis* L. pulp fiber including seeds is recovered and dried to a moisture content of less than 10 percent in a low temperature dryer having rapid air flow and with temperatures not exceeding 120 degrees Fahrenheit. Rapid drying of the seed and pulp material is important to prevent the growth of microorganisms and decay. Following drying, the seeds are separated from the pulp using a seed cleaner.

The seeds are then carefully pressed in a cold press where temperatures of the extracted oil do not exceed 120 degrees Fahrenheit. A Komet™ single or double screw expeller, Model DD85, manufactured by IBG Montforts GmbH was used. Other cold presses are commercially available and could also satisfactorily be used to extract the oil. Typically the press achieves pressures of 1200 pounds per square inch against the seed material and press head. The press may be electrically driven or driven by other mechanical means. The press cylinder, where the oil exits the press, may be enclosed within a hood and put under pressure of an inert gas such as nitrogen or carbon dioxide to prevent the freshly expelled oil from contact with oxygen to enhance the oxidative stability of the oil. To start the process no external heat is used. This is unlike other conventional pressing methods for grains and vegetable oils which add heat to the pressing head. Using a speed of 20 to 100 rpm of the Komet™ press, the oil is extracted at ambient temperatures of 70 to 90 degrees Fahrenheit. A nozzle at the press head having a round aperture ranging from 6 mm to 15 mm allows the solid seed material to be expelled from the press. The oil flows by gravity to a collection container. In one embodiment the fresh, carefully expelled oil is allowed to settle to the bottom of the container and the oil clarifies. In another embodiment the oil is collected and used in an unsettled condition. A filter can also be used for separation of the fine fiber material from the oil. The oil is then decanted for further storage and bottling.

The resulting oil is extremely high in antioxidants, as the following tables show:

TABLE 1

| Sterols | |
|---|---|
| Cholesterol | <1.0 mg/100 g |
| Campesterol | 26.2 mg/100 g |
| Stigmasterol | 10.2 mg/100 g |
| Beta Sitosterol | 461 mg/100 g |

TABLE 2

| Fatty Acid Composition of Black Raspberry Seed Oil | |
|---|---|
| Fatty Acid | grams/1.00 g |
| Myristic | nd |
| Palmitic | 1.2-1.6 |
| Palmitoleic | nd |
| Stearic | 0.1 |
| Oleic | 6.1-7.7 |
| Linoleic | 55.8-57.6 |
| Arachidonic | nd |
| Total Sat | 1.2-1.6 |
| Total MUFA | 6.1-7.7 |
| Total ω-3 FA | 35.2 |
| Total PUFA | 91.1-93.0 | nd = not detectable.
MUFA and PUFA represent mono and polyunsaturated fatty acids.
ω-3 FA = ω-3 fatty acids.

TABLE 3

| Vitamin E | |
|---|---|
| Total Tocotrienol | grams/100 g |
| Alpha Tocotrienol | <.500 mg |
| Beta Tocotrienol | 2.42 mg |
| Delta Tocotrienol | <.500 mg |
| Gamma Tocotrienol | 3.10 mg |

TABLE 4

| Total Tocopherol | grams/100 g |
|---|---|
| Alpha Tocopherol | 1.64 mg |
| Beta Tocopherol | <.500 mg |
| Gamma Tocopherol | 6.05 mg |
| Delta Tocopherol | <.500 mg |

TABLE 5

| Antioxidant Property of Black Raspberry Seed Oil | |
|---|---|
| ABTS$^+$ Scavenging Activity (μmole TE/g) | 0/3-0/7 |
| DPPH Scavenging Activity (% DPPH quenched | 11.4-53.4 |
| TPC (μg GE/g) | 35.1-92.6 |

ABTS$^+$ scavenging activity was evaluated using the radical cation generated by a chemical method.
DPPH scavenging activity was measured at a final concentration of 42 mg oil equivalent/mL or 125 μg meal equivalent/mL in the radical-antioxidant reaction mixture.
TPC = total phenolic content and is expressed as gallic acid equivalent (GE). The TPC was measured using the Folin-Ciocalteu reagent. Values were means of triplicate measurements.

Methods for Tests

Fatty Acid Analysis. One mg of each oil sample was used to prepare the fatty acid methyl esters (FAME) for gas chromatograph (GC) analysis. The GC analysis of the FA composition was performed on a HP® 6890 gas chromatograph equipped with an autosampler, Chemstation and FID (Hewlitt Packard Co., Avondale, Pa.). A fused silica capillary column SP™-2380 (30 m×0.25 mm with a 0.25 μm film thickness) from Supelco (Bellafonte, Pa.) was used with helium as the carrier gas. The following temperature program was used: 165° C. for 20 min followed by a 5°/Cmin increase to 185° C., which was then held for 10 min.

Radical Cation ABTS Scavenging Activity. Radical scavenging capacity of black raspberry antioxidant was evaluated against ABTS$^+$ generated by the chemical method. 50 μL of black raspberry antioxidants in 50% acetone was diluted with 450 μL of 7% RMCD to obtain the testing samples. ABTS$^+$ was prepared by oxidizing 5 mM aqueous solution of ABTS, 2,2'-azinobis(3-ethylbenothiazoline-6-sulfonic acid diammonium salt, with manganese dioxide at ambient temperatures for 30 minutes. The ABTS$^+$ antioxidant reaction mixture contained 1.0 mL of ABTS$^+$ with an absorbance of 0.7 at 734 nm, and 80 μL of 7% RMCD solution for the control. The absorbance at 734 nm was measured at 1 min of the reaction, and the trolox equivalent was calculated using a standard curve prepared with trolox.

Radical DPPH Scavenging Activity. Free radical scavenging capacity of black raspberry oil was determined according to the previously described procedure using the stable 2,2'-diphenyl-1-picrylhydrazyl radical (DPPH). The final concentration was 100 μM for DPPH. The absorbance at 517 nm was measured against a blank of pure ethanol at 40 and used to estimate the remaining radical levels according to a standard curve.

Total Phenolic Contents. The total phenolic content of black raspberry seed oil was determined using the Folin-Ciocalteu reagent. In brief, the reaction mixture contained 50 μL of the Folin-Ciocalteu reagent freshly prepared in the laboratory and 0.75 mL of 20% sodium carbonate and 3 mL of pure water. After two hours of reaction at ambient temperature, the absorbance at 765 nm was measured and used to calculate the phenolic contents using gallic acid as a standard.

As indicated above, black raspberry oil has very high concentrations of total vitamin E, tocotrienol, and tocopherols, even higher that other fruit oils from cranberry and grape. Tocotrienols are increasingly being recognized as having an important role in preventing degenerative diseases. Gamma tocopherol, the most potent antioxidant of all the tocopherols is higher in black raspberry oil than in cranberry oil and contributes to oxidative stability of the unsaturated oils in black raspberry oil. The presence of high concentrations of both tocotrienol and tocopherols is unusual as other vegetable oils are more typically high in either tocotrienol or tocopherol but not both.

In another embodiment the oil can be extracted from the raw plant material using Super Critical Fluid Extraction technology. Super Critical Fluid Extraction uses $CO_2$ under pressure to enter the cell walls of the plant material to force the separation of oils and extracts. By varying temperature and pressure different separations or fractions can be achieved. Because the process works at low temperature and in the absence of oxygen, the resulting oil is of high quality and unaltered from its natural form. While black raspberry oil appears to be the most promising, it should be mentioned that other natural oils such as those derived from black cumin seed, caneberries (raspberry, blackberry, marionberry, boysenberry and evergreen blackberry), coriander, sea buckthorn, palm fruit oil and cardomon are also known to be high in antioxidants. Finally, combinations of the various oils discussed above are also contemplated by the invention and are therefore within its scope.

I. Murine Hepatic Metastases from Adenocarcinoma Cells.

The following paragraph is for background information only and is not intended to constitute an admission of prior art.

Experimental data was reported in Saltzman, Heise, Hasz, Zebede, Kelly, Curtiss, Leonard, and Anderson, "Attenuated *Salmonella typhimurium* Containing Interleukin-2 Decreases MC-38 Hepatic Metastases: a Novel Anti-Tumor Agent," *Cancer Biotherapy and Radiopharmaceuticals* 11:2 (1996). At the time, it was believed that the plamid pIL2 contained DNA (SEQ ID NO: 6) encoding normal interleukin-2 (SEQ ID NO: 3). However, it was recently discovered that the DNA (SEQ ID NO: 5) in the plasmid pIL2 contained a single basepair deletion encoding a truncated protein (SEQ ID NO: 2). This was recently noted in Sorenson, Banton, Frykman, Leonard, and Saltzman, "Attenuated *Salmonella typhimurium* with IL-2 Gene Reduces Pulmonary Metastases in Murine Osteosarcoma," *Clin Orthop Relat Res* (2008) 466: 1285-1291. Neither of the above-noted publications discloses the nucleotide sequence (SEQ ID NO:1) for the truncated DNA or the amino acid sequence (SEQ ID NO:2) for the truncated protein.

The following discussion refers to the truncated DNA and protein.

Two basic tumor models were used to examine the efficacy of this novel anti-tumor system on hepatic metastases from adenocarcinoma cells: a Tumor Treatment Model and a Tumor Prevention Model.

In the Tumor Treatment Model female 6 to 8 week old C57BL/6 mice were purchased from Harlan Sprague-Dawley (Indianapolis, Ind.). At the onset of each experiment, the mice were randomly divided into four groups (Control, *Salmonella typhimurium*-IL-2, antioxidant oil alone and *Salmonella typhimurium* IL-2 with antioxidant oil) that were orally inoculated with saline or $10^8$ *S. typhimurium* $\chi$4550pIL2 and received a standard rodent diet or a standard rodent diet supplemented with antioxidant oil for the duration of the experiment. The procedure yielded four groups: saline, antioxidant oil, *S. typhimurium* $\chi$4550pIL2, and *S. typhimurium* $\chi$4550pIL2+ antioxidant oil. Mice in the antioxidant oil and *S. typhimurium* $\chi$4550pIL2+ antioxidant oil groups received a standard rodent diet supplemented with black raspberry seed oil from Botanic Oil Innovation, Inc. (Spooner, Wis.) at a concentration of ten percent by weight. In order to incorporate the antioxidant oil into the diet, it was necessary to crush the standard rodent diet pellets to the consistency of coarse sand. To negate any possible variation in food consumption due to the form of the diet, all groups received a crushed diet. Mice were fed their respective diets and water ad libitum. 25,000-100,000 MCA murine adenocarcinoma cells were injected into the spleen to facilitate hepatic metastases via the portal circulation on Day 0. On Day 3 the mice were randomized into their groups and treated. On Day 12 of experimentation, mice were sacrificed and liver metastases were enumerated for number and volume of tumor.

In the Tumor Prevention Model, at the onset of each experiment, mice were administered the control (saline), antioxidant oil, *S. typhimurium* $\chi$4550pIL2 with and without the antioxidant oil on Day 0. On Day 7 splenic injection of 50,000 MCA-38 adenocarcinoma cells was accomplished. On Day 14 hepatic metastases were enumerated for tumor number and volume. Total tumor volume was calculated assuming tumor shape as a sphere ($4/3\ r^3$). Hepatic lymphocytes were also analyzed from each experimental.

Experiments were concluded at 3, 7 or 14 days following oral inoculation and all mice were sacrificed under anesthesia. A splenectomy was performed to allow for splenic lymphocyte analysis. Splenic lymphocytes were prepared by modifying a technique used to isolate hepatic lymphocytes. Briefly, the spleen was mechanically minced, passed through 100-gauge nylon mesh (Sefar America, Inc., Kansas City, Mo.), and suspended in DMEM (Sigma, St. Louis, Mo.) with 10% fetal goat serum (Sigma). Individual specimens were place on lymphocyte separation medium (Mediatech, Inc., Herndon, Va.) and centrifuged at 300 g for 60 minutes at room temperature. The mononuclear cell layer was harvested and washed twice in phosphate buffered solution (Gibco, Grand Island, N.Y.) with centrifugation at 300 g for 10 minutes at room temperature.

Splenic lymphocytes were stained with a combination of fluorochrome-conjugated anti-mouse monoclonal antibodies, including anti-NK1.1, anti-CD4, and anti-CD8 (all obtained from BD Biosciences Pharmingen, San Diego, Calif.). Lymphocyte staining was performed at 4° C. for 30 minutes by incubating the cells with monoclonal antibodies. After washing, analysis was performed with a FACScan cytofluorometer (Becton-Dickinson, Grenoble, France) using CellQuest software (Becton-Dickinson). Viable lymphocytes were gated by side and forward scatter profiles. For each specimen, analysis was based on 10,000 acquired events.

Statistical analyses were performed using StatView 5.0 (SAS Institute, Cary, N.C.). At the conclusion of an experiment, splenic lymphocyte phenotype was analyzed by analysis of variance followed by Fisher's test for significant difference. Experiments were repeated twice on separate days to verify reproducibility. Statistical significance was regarded as $P<0.05$.

Examples

Tumor Treatment Model

Figure 4:
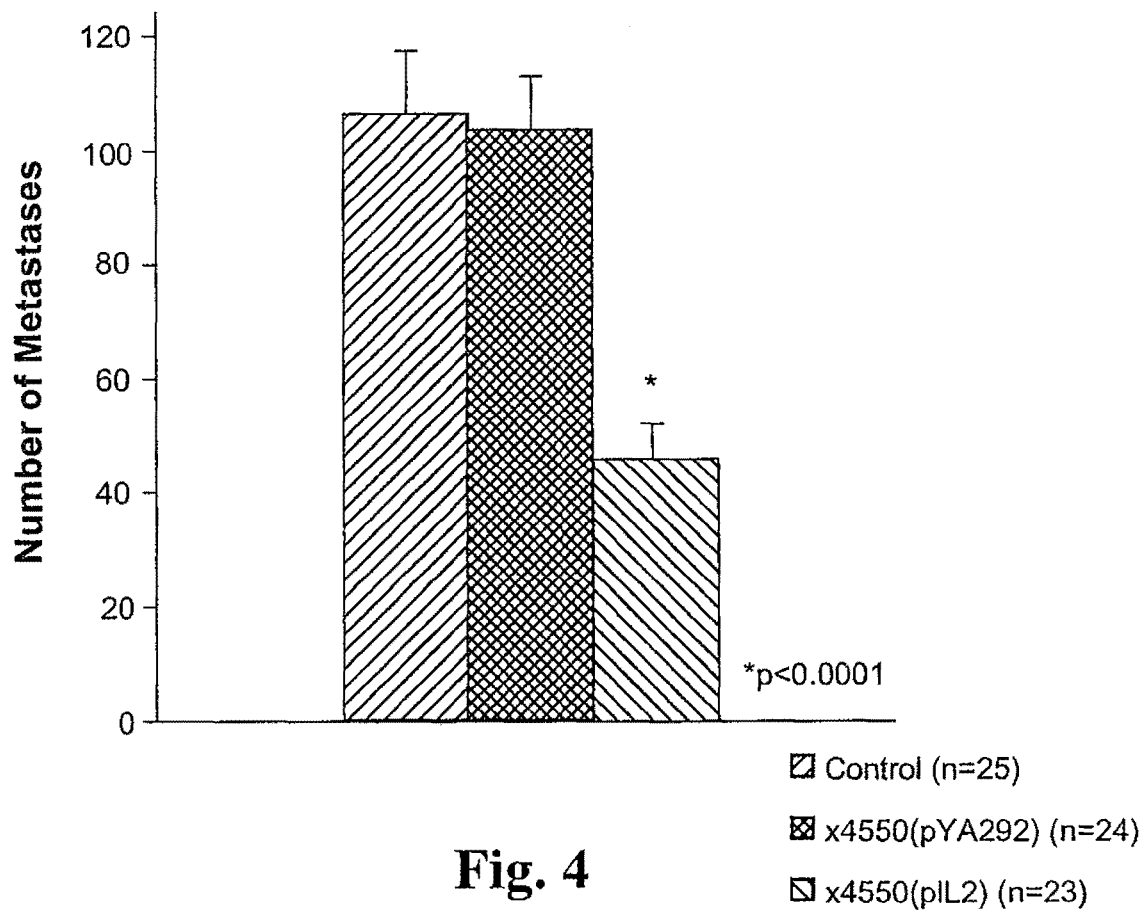
FIG. 4 is a bar graph representing (Tumor Treatment Model) reduced hepatic metastases in response to control (saline), *Salmonella typhimurium* χ4550 and *Salmonella typhimurium* χ4550pIL2 with the truncated human IL-2 gene.

FIG. 4 shows the results of the control, *S. typhimurium* $\chi$4550 and *S. typhimurium* $\chi$4550pIL2 groups on hepatic metastases when administered orally to tumor burdened mice. A statistically significant decrease in hepatic colorectal metastases is shown. There was a mean of 106.4 metastases in the control group, a mean of 103.7 metastases in the group fed bacteria without the gene for truncated IL-2, and a mean of 44.3 metastases in the group fed bacteria with the gene for truncated IL-2.

Figure 5:
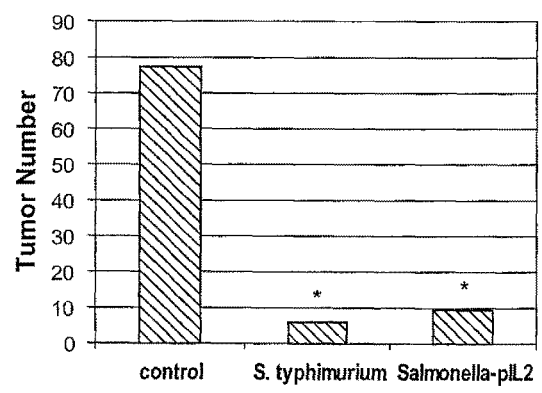
FIG. 5 shows a bar graph representing (Tumor Treatment Model) reduced hepatic tumor number in response to control (saline), *Salmonella typhimurium* χ4550 and *Salmonella typhimurium* χ4550pIL2 with the truncated human IL-2 gene.

FIG. 5 shows additional results of the control, *S. typhimurium* $\chi$4550 and *S. typhimurium* $\chi$4550pIL2 groups on tumor number when administered orally to tumor burdened mice. A statistically significant reduction in tumor number is shown.

Figure 6:
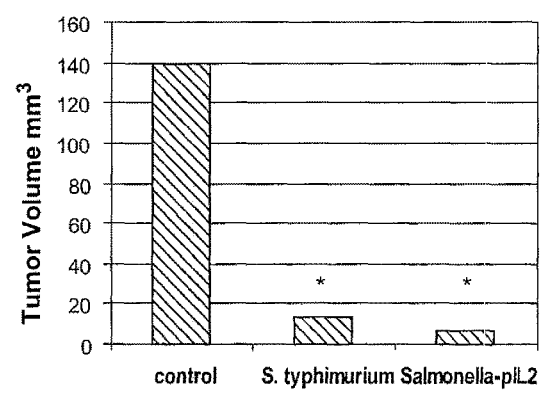
FIG. 6 shows a bar graph representing (Tumor Treatment Model) reduced hepatic tumor volume in response to control (saline), *Salmonella typhimurium* χ4550 and *Salmonella typhimurium* χ4550pIL2 with the truncated human IL-2 gene.

FIG. 6 shows the results of the control, *S. typhimurium* $\chi$4550 and *S. typhimurium* $\chi$4550pIL2 groups on tumor volume when administered orally to tumor burdened mice. A statistically significant reduction in tumor volume is shown.

Figure 7:
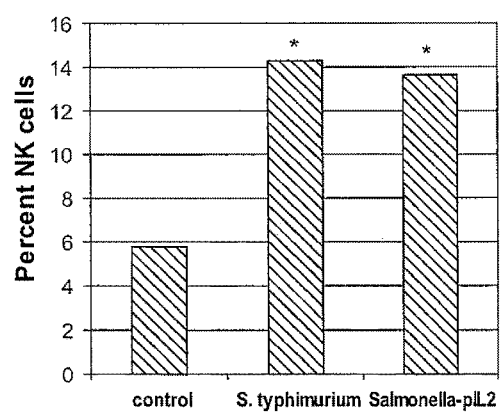
FIG. 7 shows a bar graph representing (Tumor Treatment Model) elevated hepatic NK cells in response to control (saline), *Salmonella typhimurium* χ4550 and *Salmonella typhimurium* χ4550pIL2 with the truncated human IL-2 gene.

FIG. 7 shows the results of the control, *S. typhimurium* $\chi$4550 and *S. typhimurium* $\chi$4550pIL2 groups on NK cells when administered orally to tumor burdened mice. An increase in NK cells is shown in the *S. typhimurium* $\chi$4550 and *S. typhimurium* $\chi$4550pIL2 groups when compared to the control group.

Figure 8:
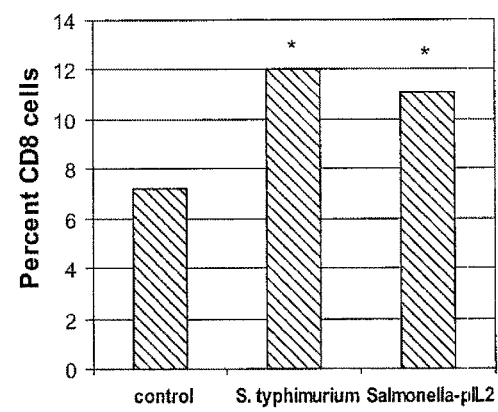
FIG. 8 shows a bar graph representing (Tumor Treatment Model) elevated hepatic CD8+ cells in response to control (saline), *Salmonella typhimurium* χ4550 and *Salmonella typhimurium* χ4550pIL2 with the truncated human IL-2 gene.

FIG. 8 shows the results of the control, *S. typhimurium* $\chi$4550 and *S. typhimurium* $\chi$4550pIL2 groups on CD8+ cells when administered orally to tumor burdened mice. An increase in CD8+ cells is shown in the *S. typhimurium* χ4550 and *S. typhimurium* χ4550pIL2 groups when compared to the control group.

Figure 9:
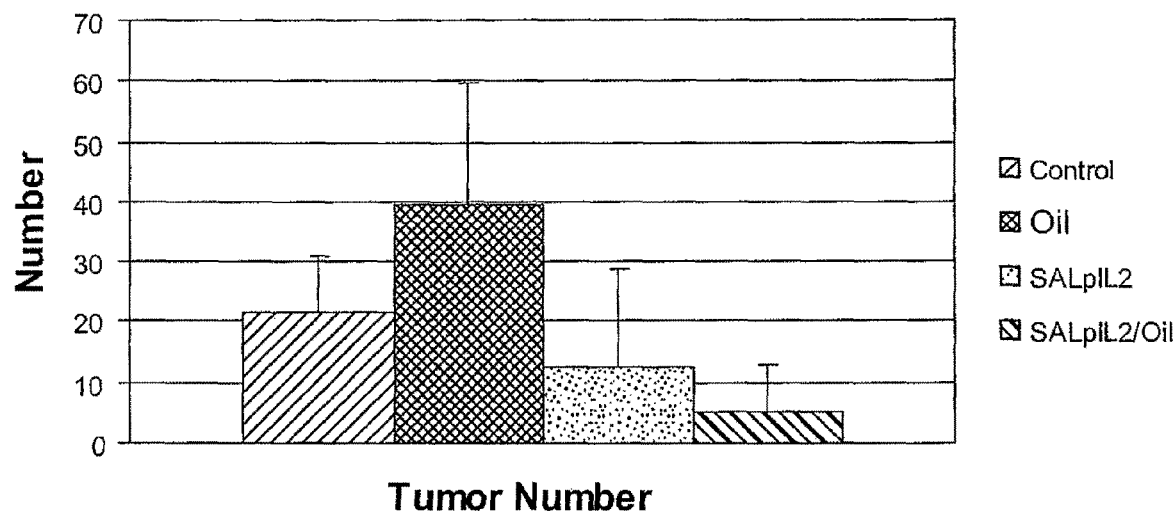
FIG. 9 shows a bar graph representing (Tumor Treatment Model) reduced tumor number in response to saline, antioxidant oil, *Salmonella typhimurium* χ4550pIL2 and *Salmonella typhimurium* χ4550pIL2 with the truncated human IL-2 gene plus antioxidant oil.

FIG. 9 shows the results of the four groups (control, oil, *S. typhimurium* χ4550pIL2 and *S. typhimurium* χ4550pIL2 plus antioxidant oil on total tumor number in tumor burdened mice. As shown, the *S. typhimurium* χ4550pIL2 plus antioxidant oil group had approximately an eight fold reduction in total number of tumor cells compared to the group receiving only oil. An approximate two fold reduction in the number of tumors was shown compared to the group receiving only *S. typhimurium* χ4550pIL2. Compared to the control group, the group receiving *S. typhimurium* χ4550pIL2 plus antioxidant oil showed a four fold reduction in the number of tumors.

Figure 10:
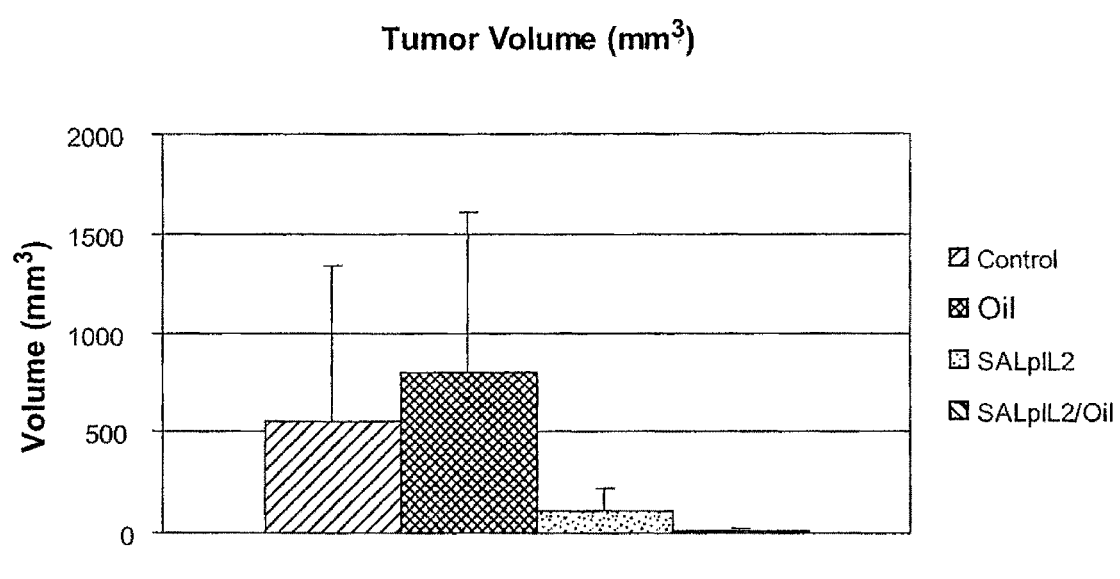
FIG. 10 shows a bar graph representing. (Tumor Treatment Model) reduced tumor volume in response to control (saline), antioxidant oil, *Salmonella typhimurium* χ4550pIL2 and *Salmonella typhimurium* χ4550pIL2 with the truncated human IL-2 gene plus antioxidant oil.

FIG. 10 shows the results of the four groups (control, antioxidant oil, *S. typhimurium* χ4550pIL2 and *S. typhimurium* χ4550pIL2+ antioxidant oil) on tumor volume in tumor burdened mice. As shown the *S. typhimurium* χ4550pIL2 plus antioxidant oil group showed almost negligible tumor volume compared to the antioxidant oil only group, the control group, and the *S. typhimurium* χ4550pIL2 only group.

Examples

Tumor Prevention Model

Figure 11:
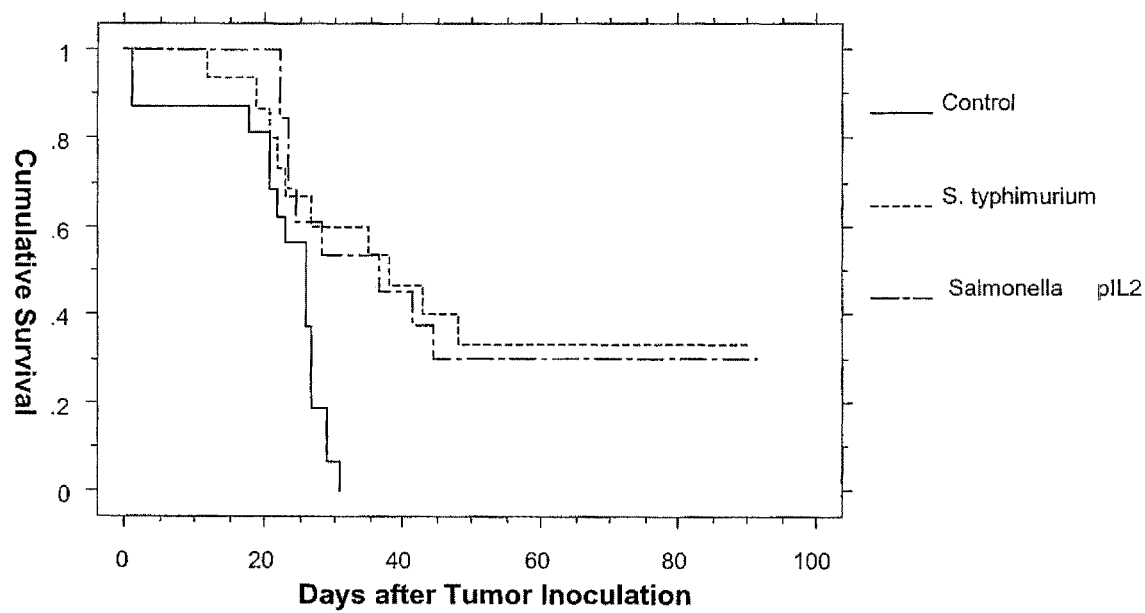
FIG. 11 shows a graph representing (Tumor Prevention Model) improved long term survival in response to control (saline), *Salmonella typhimurium* χ4550 and *Salmonella typhimurium* χ4550pIL2 with the truncated human IL-2 gene.

FIG. 11 shows the cumulative survival of tumor naive mice after being fed control, *S. typhimurium* χ4550 and *S. typhimurium* χ4550pIL2, The groups receiving *S. typhimurium* χ4550 and *S. typhimurium* χ4550pIL2 show an almost 40% long term survival rate over the control group.

Figure 12:
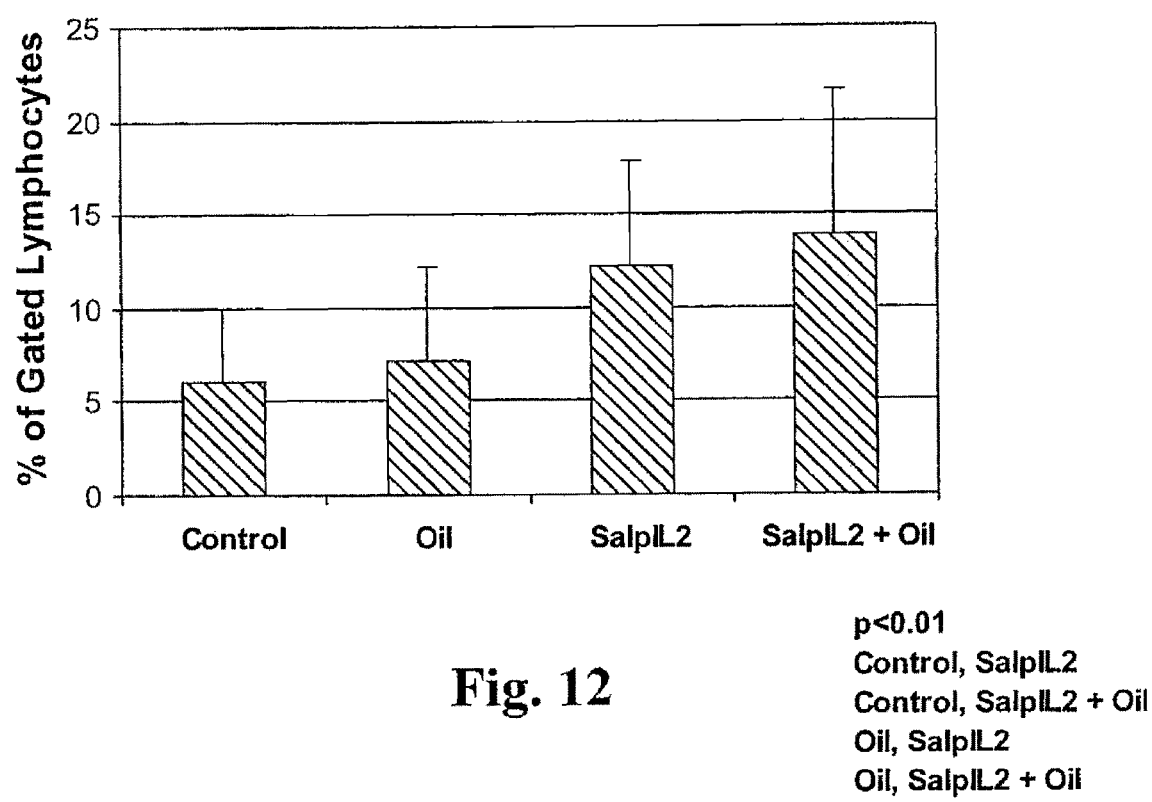
FIG. 12 shows a bar graph representing (Tumor Prevention Model) increased NK cell population in response to control (saline), antioxidant oil, *Salmonella typhimurium* χ4550pIL2 and *Salmonella typhimurium* χ4550pIL2 with the truncated human IL-2 gene plus antioxidant oil.

FIG. 12 shows the results of the four groups (control, antioxidant oil, *S. typhimurium* χ4550pIL2 and *S. typhimurium* χ4550pIL2 plus antioxidant oil) on NK cell population in tumor naive mice. A statistically significant increase over the control group and antioxidant oil only group is shown in the *S. typhimurium* χ4550pIL2 and *S. typhimurium* χ4550pIL2 plus antioxidant oil groups.

Figure 13:
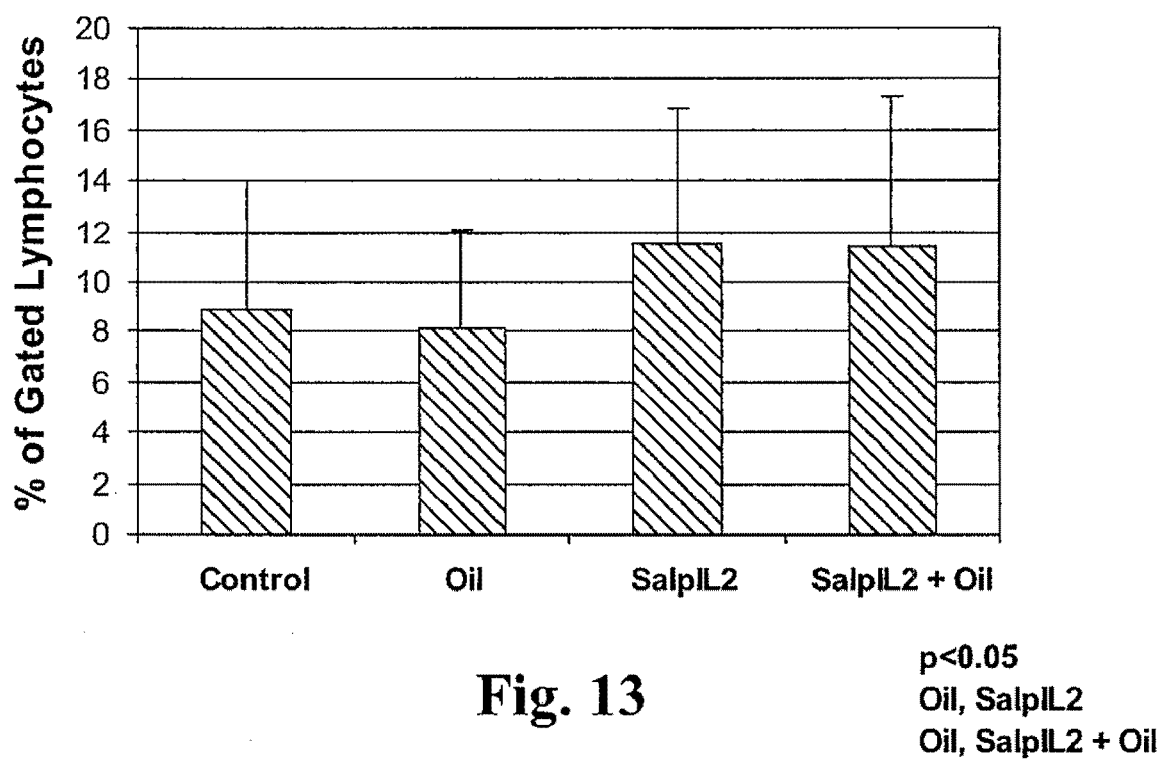
FIG. 13 shows a bar graph representing (Tumor Prevention Model) CD8+ cell, population in response to control (saline), antioxidant oil, *Salmonella typhimurium* χ4550pIL2 and *Salmonella typhimurium* χ4550pIL2 with the truncated human IL-2 gene plus antioxidant oil.

FIG. 13 shows the results of the four groups (control, antioxidant oil, *S. typhimurium* χ4550pIL2 and *S. typhimurium* χ4550pIL2 plus antioxidant oil) on CD8+ cell population in tumor naive mice. A slight increase in CD8+ T cell population is shown in the mice in the *S. typhimurium* χ4550pIL2 plus antioxidant oil group.

Figure 14:
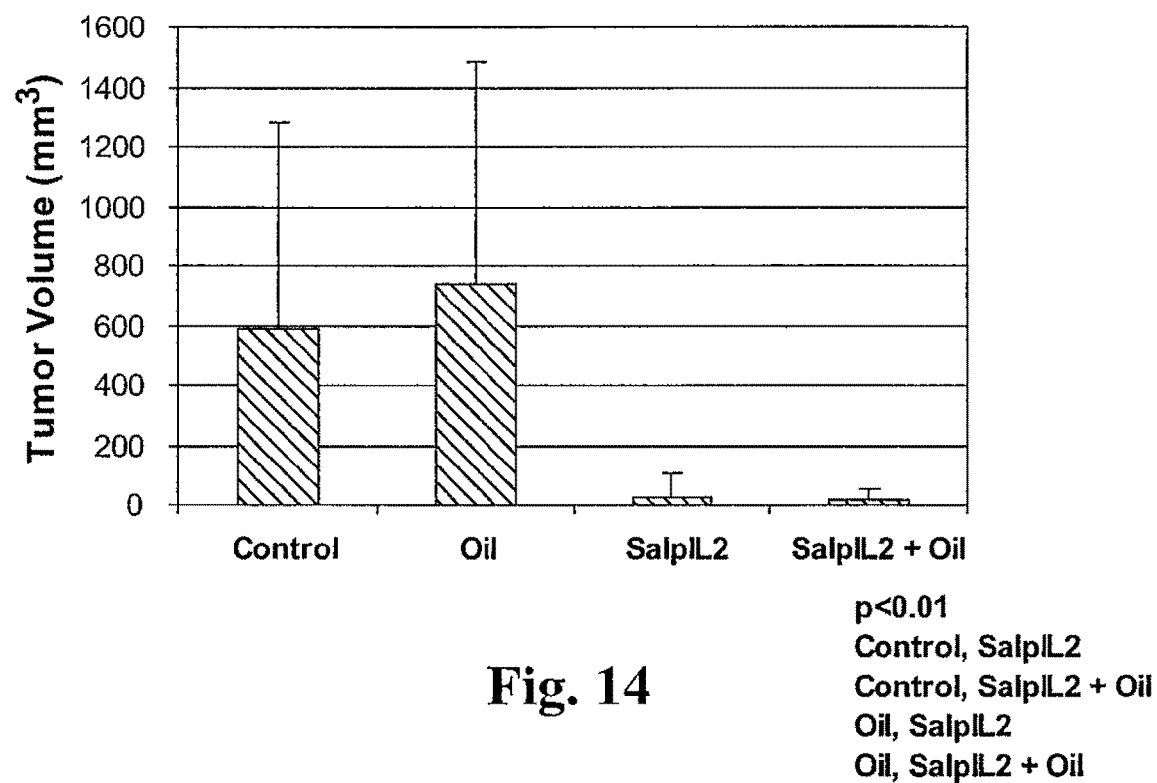
FIG. 14 shows a bar graph representing (Tumor Prevention Model) CD4+ T helper cell population in response to control (saline), oil, *Salmonella typhimurium* χ4550pIL2 and *Salmonella typhimurium* χ4550pIL2 with the truncated human IL-2 gene plus antioxidant oil.

FIG. 14 shows the results of the four groups (control, antioxidant oil, *S. typhimurium* χ4550pIL2 and *S. typhimurium* χ4550pIL2 plus antioxidant oil) on CD4+ T helper cell population in tumor naive mice. An overall statistically significant increase in CD4+ T helper cell population is shown in the *S. typhimurium* χ4550pIL2 plus antioxidant oil group.

Figure 15:
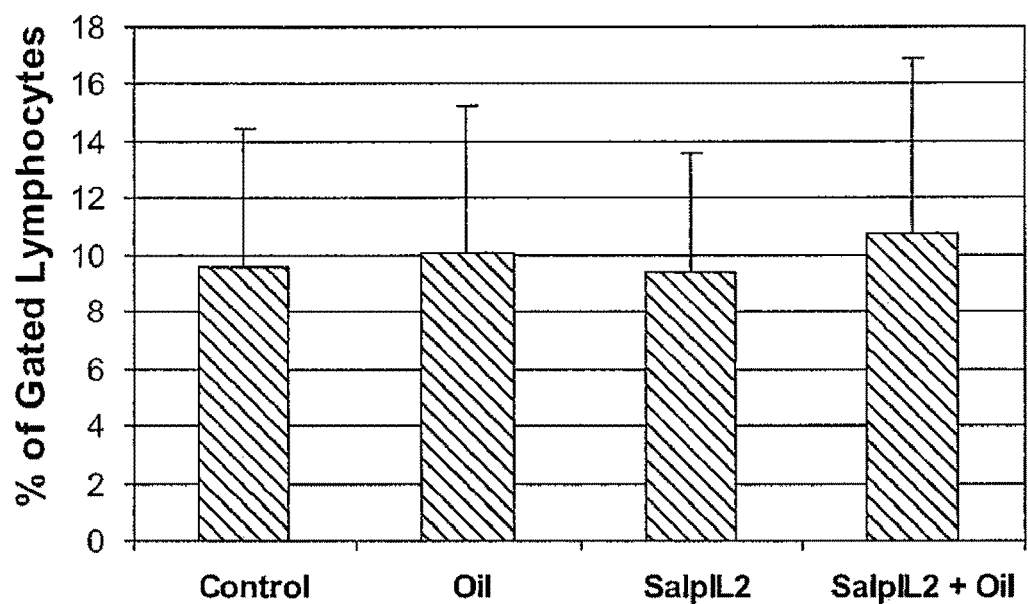
FIG. 15 shows a bar graph representing (Tumor Prevention Model) tumor number in response to control (saline), antioxidant oil, *Salmonella typhimurium* χ4550pIL2 and *Salmonella typhimurium* χ4550pIL2 with the truncated human IL-2 gene plus antioxidant oil.

FIG. 15 shows the results of the four groups (control, antioxidant oil, *S. typhimurium* χ4550pIL2 and *S. typhimurium* χ4550pIL2 plus antioxidant oil) on tumor number in tumor naive mice. A statistically significant decrease in tumor number is shown in the *S. typhimurium* χ4550pIL2 and *S. typhimurium* χ4550pIL2 plus antioxidant oil groups.

Figure 16:
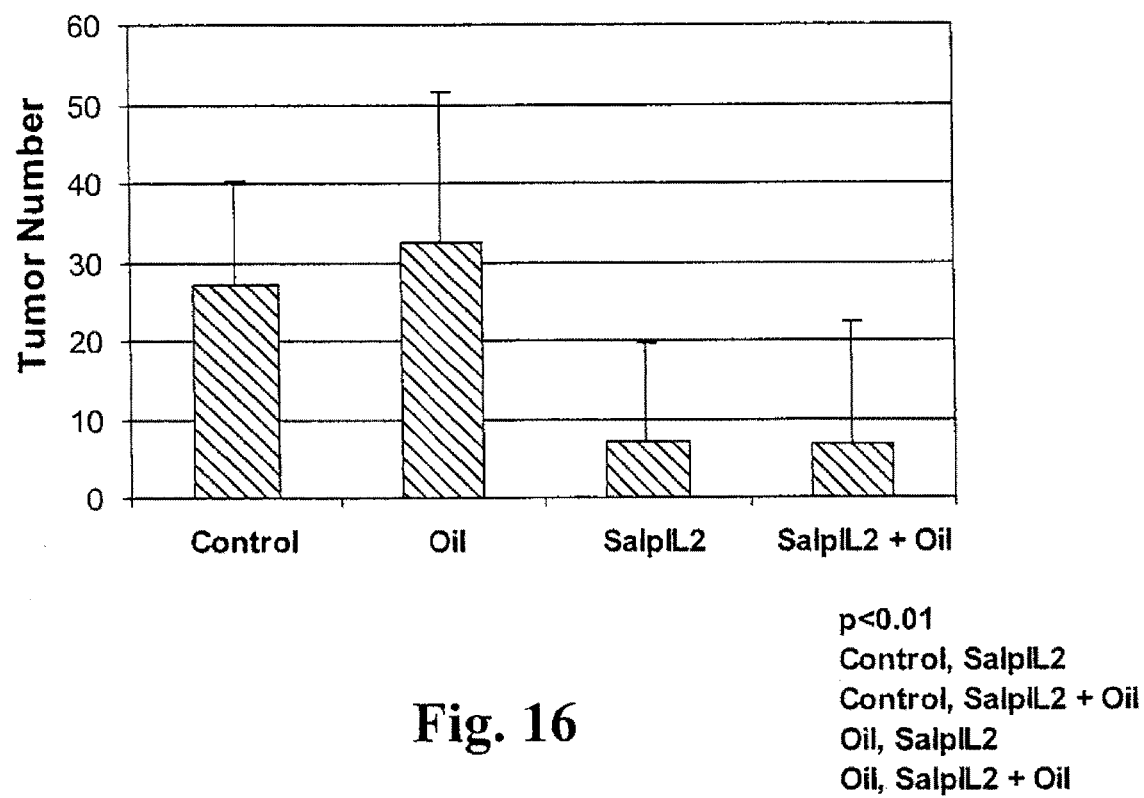
FIG. 16 shows a bar graph representing (Tumor Prevention Model) tumor volume in response to control (saline), antioxidant oil, *Salmonella typhimurium* χ4550pIL2 and *Salmonella typhimurium* χ4550pIL2 with the truncated human IL-2 gene plus antioxidant oil.
Figure 17:
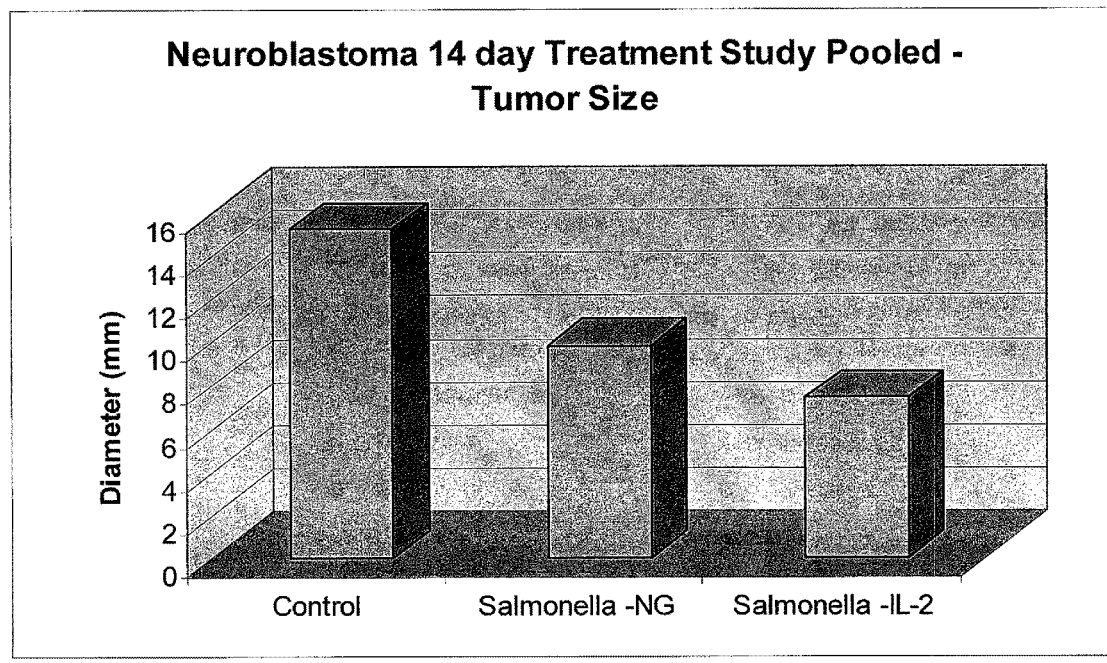
FIG. 17 shows is a bar graph showing the reduction in tumor size of retroperitoneal neuromblastoma in control (saline), *Salmonella typhimurium* χ4550 and *Salmonella typhimurium* χ4550pIL2 with the truncated human IL-2 gene.

FIG. 16 shows the results of the four groups (control, antioxidant oil, *S. typhimurium* χ4550pIL2 and *S. typhimurium* χ4550pIL2 plus antioxidant oil) on tumor volume in tumor naive mice. A statistically significant decrease in tumor volume is observed in the *S. typhimurium* χ4550pIL2 group, with a further decrease observed in the *S. typhimurium* χ4550pIL2 antioxidant oil group.

Treatment of Retroperitoneal Neuroblastoma.

The following paragraph is for background information only and is not intended to constitute an admission of prior art.

Experimental data was reported in Daniel A. Saltzman, "Cancer Immunotherapy based on the Killing of *Salmonella typhimurium*-infected Tumour Cells," Expert Opin. Biol. Ther. (2005) 5(4): 443-449. At the time, it was believed that the plamid pIL2 contained DNA (SEQ ID NO: 6) encoding normal interleukin-2 (SEQ ID NO: 7). However, it was recently discovered that the DNA in the plasmid pIL2 was actually a single base-pair deleted DNA (SEQ ID NO:5) encoding a truncated protein (SEQ ID NO: 2). This was recently noted in Sorenson, Banton, Frykman, Leonard, and Saltzman, "Attenuated *Salmonella typhimurium* with IL-2 Gene Reduces Pulmonary Metastases in Murine Osteosarcoma," *Clin Orthop Relat Res* (2008) 466: 1285-1291. Neither of the above-noted publications discloses the nucleotide sequence (SEQ ID NO:1) for the truncated DNA or the amino acid sequence (SEQ ID NO:2) for the truncated protein.

The following data are for the truncated DNA and protein.

Neuroblastoma is the most common malignancy in infants and the most common extracranial solid tumor of childhood. Infants and children with confined disease have a >80% chance of cure, whereas older children with metastatic disease have only a 20-25% cure rate. Although neuroblastoma accounts for only ~10% of all childhood tumors, it is responsible for 15% of all cancer-related deaths in the pediatric age group. Multiple therapies are being studied to treat these children with state IV disease, including radioactive iodine-131-meta-iodobenzylguanidine (MIBG) therapy, antiobiotics directed at the ganglioside GD2, and 13-cis-retinoic acid therapy combined with chemotherapy. These therapies have shown inconsistent response rates towards treatment, and ongoing studies continue to delve into their utility.

Figure 18:
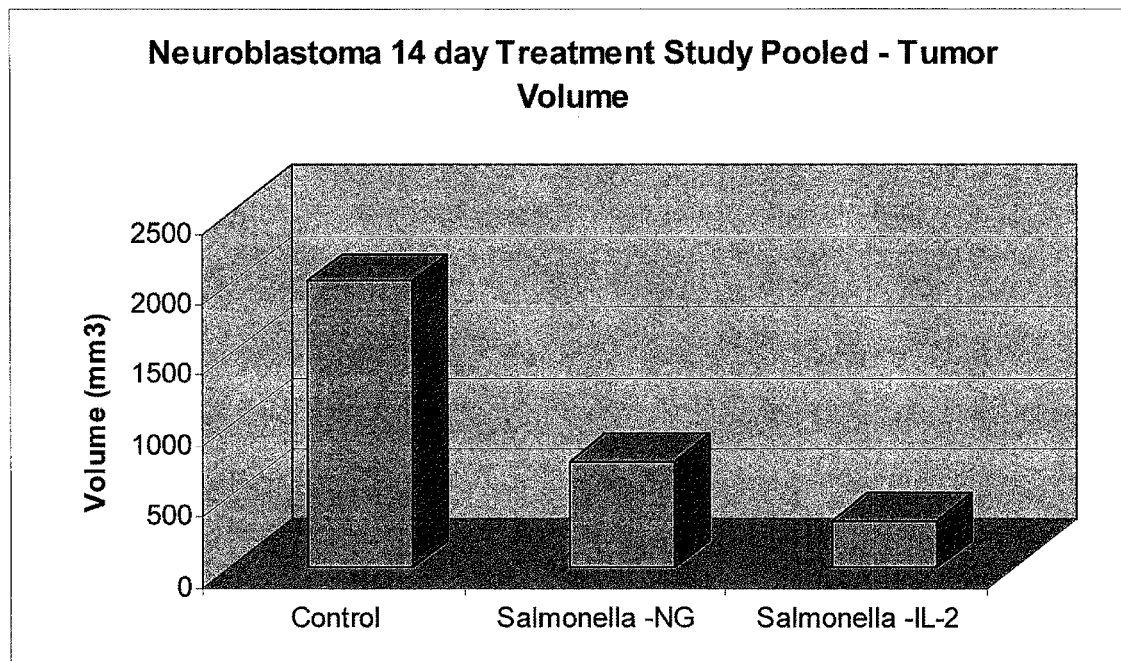
FIG. 18 is a bar graph showing the reduction in tumor volume of retroperitoneal neuromblastoma in control (saline), *Salmonella typhimurium* χ4550 and *Salmonella typhimurium* χ4550pIL2 with the truncated human IL-2 gene.
Figure 19:
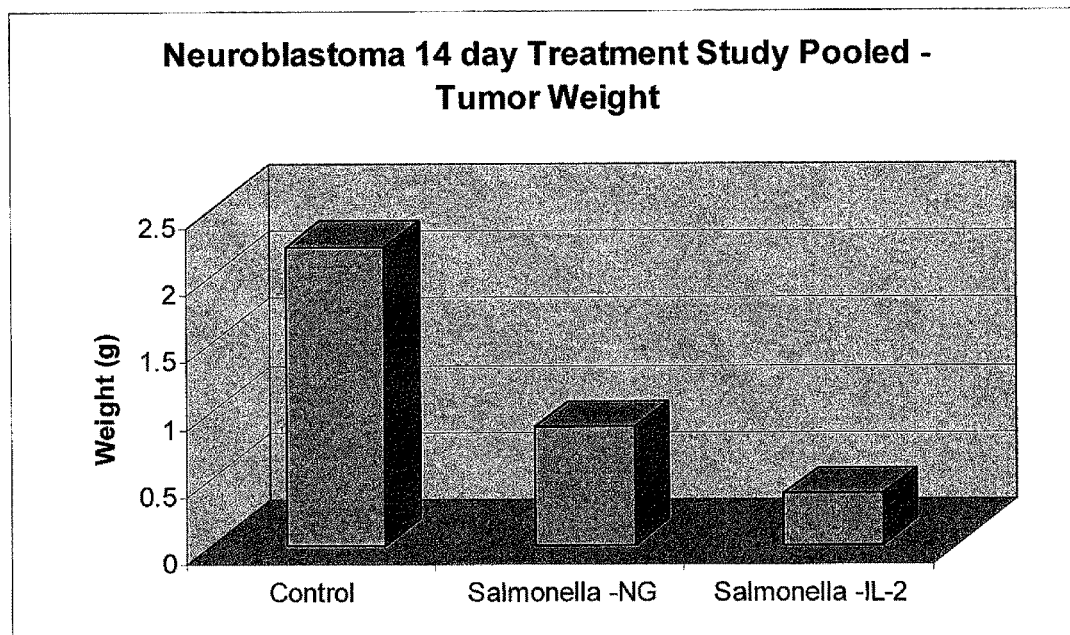
FIG. 19 is a bar graph showing the reduction in tumor weight of retroperitoneal neuromblastoma in control (saline), *Salmonella typhimurium* χ4550 and *Salmonella typhimurium* χ4550pIL2 with the truncated human IL-2 gene.

Due to the finding of an increase of *Salmonella* invasion and division efficiency in neuroblastoma cells, the antitumor effect of *Salmonella* in a preclinical murine model of a retroperitoneal neuroblastoma was studied. In these experiments, it was found that treatment with *S. typhimurium* or *Salmonella*-pIL2 in those mice with retroperitoneal neuroblastomata resulted in a significant reduction in tumor volume (749.5 and 332.4 mm3, respectively) when compared with saline controls (2024.3 mm3; p<0.00001) (FIG. 18). Treatment with *S. typhimurium* or *Salmonella*-pIL2 is also associated with a reduction in tumor weight (0.88 and 0.377 grams, respectively) when compared with saline controls (2.218 grams; p<0.0001) (FIG. 19). When comparing reductions between *S. typhimurium* and *Salmonella*-pIL2 treated animals, there is a decrease in tumor volume (749.5 and 332.4 mm3; p<0.0001) and in tumor weight (0.88 and 0.377 grams; p<0.0001), which are both statistically significant. Treatment with *S. typhimurium* and *Salmonella*-pIL2 results in a reduction in tumor burden (63 and 84%, respectively) in animals with retroperitoneal neuroblastoma.

Prevention and Treatment of Pulmonary Metastases in Murine Osteosarcoma.

Brent S. Sorenson, Kaysie L. Banton, Natalie L. Frykman, Arnold S. Leonard, Daniel A. Saltzman, "*Attenuated Salmonella typhimurium with Interleukin 2 Gene Prevents the Establishment of Pulmonary Metastases in a Model of Osteosarcoma,*" *Journal of Pediatric Surgery* (2008) 43, 1153-1158; "Attenuated Salmonella typhimurium with IL-2 Gene Reduces Pulmonary Metastases in Murine Osteosarcoma," *Clin Orthop Relat Res* (2008) 466:1285-1291.

Osteosarcoma is the most common primary bone cancer, with approximately 900 new cases annually in the United States. There is a peak incidence in early adolescence correlated with pubertal bone growth and a second peak after age 50. Primary tumors develop in the distal femur and proximal tibia and humerus. Current management of primary osteosarcoma involves surgical resection with wide margins or limb amputation in conjunction with pre- and postoperative neoadjuvant chemotherapy. Survival from local disease has improved from 20% in 1970 to approximately 70% at 3 years with the advent of current treatment with high-dose methotrexate, cisplatin, ifosfamide, and doxorubicin. Despite the dramatic enhancement in patients' event free survival, toxicity affects nearly all patients treated with these therapies. However, in patients who present with metastatic disease detectable by CT, less than 30% disease-free survival has been achieved. In some cases, intravenous interleukin-2 treatment has resulted in complete regression of the primary tumor, though severe side effects have been noted, including fever, nausea, capillary leak syndrome, and death.

We demonstrated a single oral dose of an attenuated *Salmonella typhimurium* genetically engineered with a gene for a truncated human interleukin-2 (SalpIL2) substantially reduces unresectable adenocarcinoma metastases to the liver in experimental treatment and prophylactic mouse models. In addition, SalpIL2 reduces the volume and mass of retroperitoneal neuroblastoma tumors in an experimental murine treatment model. Interestingly, the *Salmonella* species of bacteria also have a unique propensity to colonize tumor cells. In vitro experiments have demonstrated the ability of SalpIL2 to invade and divide preferentially within K7M2 osteosarcoma cells with respect to primary murine hepatocytes. Thus SalpIL2 may be able to persist for long periods in malignant tissues providing a prolonged antigen presentation state and enhanced immune response in the region.

Based on our previous observations, we hypothesize SalpIL2 would substantially reduce osteosarcoma pulmonary metastases by increasing splenic and local NK cell populations in this newly developed experimental model.

Materials and Methods
1. Reduction of Pulmonary Metastases after Injection with Murine Osteosarcoma Cells.

In triplicate experiments, 45 balb/c mice were administered murine K7M2 osteosarcoma cells by tail vein injection. Three days later, animals were orally gavaged saline or attenuated *Salmonella* species; they were then euthanized on day 21 for tumor enumeration, volume, and assessment of systemic NK and T cell populations. In an additional experiment, animals were harvested for pulmonary lymphocyte analysis.

Attenuated *S. typhimurium* v4550 and plasmid pYA292 were a gift from Dr. Roy Curtiss III, Washington University, St. Louis, Mo. v4550 was attenuated by Tn10 transposon mutagenesis to remove adenylate cyclase (cya), cyclin adenosine monophosphate receptor protein (crp), and aspartate semialdehyde dehydrogenase (asd) genes from the bacterial genome. These mutants have virulence factors removed, but retain immunogenic properties. Plasmid constructs with and without the truncated gene for human interleukin-2 (SalpIL2) were electroporated into v4550 using well-described techniques and renamed SalpIL2 and Sal-NG [28]. Standardized glycerol stocks of approximately $10^8$ CFU/mL were prepared by creating growth curves for overnight cultures in Luria broth (Difco Laboratories, Detroit, Mich.) and freezing aliquots with an $O.D._{600}$ of 0.160 in liquid nitrogen. For experiments, cryovials were thawed to room temperature, serially diluted, and plated on MacConkey agar plates to verify CFU concentration. Use of *S. typhimurium* with a gene for a truncated human interleukin-2 was approved by the University of Minnesota Institutional Biosafety Committee (numbers 541 and 542).

Female balb/c mice 6 to 8 weeks old were acquired from Harlan Sprague Dawley (Indianapolis, Ind.) and housed in microisolator cages, fed standard mouse chow and water ad libitum, and given 12 hours light/dark cycles under the strict care of the University of Minnesota Research Animal Resources.

The murine osteosarcoma cell line K7M2 was acquired from the American Type Culture Collection and maintained in 25 mL DMEM, 10% fetal bovine serum, 1% penicillin, streptomycin, and L-glutamine (Sigma Chemical, St. Louis, Mo.) at 37° C. at 5% $CO_2$. Media was changed twice weekly and cells were not allowed to become confluent. Tumor cells were incubated with 0.3% trypsin EDTA (Invitrogen, Carlsbad, Calif.) at 37° C. at 5% $CO_2$ for 3 minutes or until non-adherent. Cells were serially washed in Hanks' balanced salt solution (HBSS, Invitrogen) before enumeration via trypan blue exclusion (Sigma Chemical) on a phase contrast hemocytometer (Hausser Scientific, Horsham, Pa.). The suspension was diluted to a concentration of $2 \times 10^6$ cells per mL and placed on ice prior to injection. All tumor preparations were more than 90% viable and used within 1 hour of preparation.

We developed a model for pulmonary metastases for these experiments. Similar techniques have been implemented for quantifying the metastatic potential of the K7M2 cell line. In triplicate experiments, animals were anesthetized by intraperitoneal injection of 2:1 xylazine 20 mg/mL (Phoenix Pharmaceuticals, St. Joseph, Mo.) and ketamine 100 mg/mL (Abbot Laboratories, North Chicago, Ill.). The animals' eyes were swabbed with Betadine ophthalmic eye ointment (Purdue Pharma LP, Stamford, Conn.) and the animals were placed in a Broome odent Holder (Kent Scientific, Torrington, Conn.). Tails were incubated for one minute in 47° C. Betadine solution (Purdue Pharma LP) to allow for vasodilatation of the left lateral tail vein and scrubbed with a 70% ethanol swab before 200,000 K7M2 cells were injected into the left lateral tail vein. Mice were placed at random in cages with microisolators and placed on a warming pad for 2 hours or until animals were walking. On Day 3, mice were orally gavaged with their respective treatments (n=5), 200 µL HBSS for controls or $3 \times 10^7$ CFU of either Sal-NG or SalpIL2. In all experiments the mice were evaluated for presence of metastases 3 weeks after injection by euthanasia followed by an intratracheal injection of 1.5 mL of 15% India-ink solution via a blunt-ended needle. The stained lungs were carefully resected and rinsed in Fekete's solution (300 mL 70% ethanol, 30 mL 37% formaldehyde, 5 mL glacial acetic acid) and then placed in fresh Fekete's solution overnight in a 60×15 mm tissue culture dish. Tumors were enumerated, their diameters were measured and volume was calculated by $4/3\pi r^3$, assuming the metastases were spherical. Spleens were aseptically removed and placed in 60×15 mm culture dishes for FACS analysis of splenic lymphocytes. Due to inability to collect pulmonary lymphocytes or perform histopathological analysis from Fekete stained lungs, two additional experiments with 25 mice were conducted. Lungs for histopathological analysis were aseptically removed and placed in 10% formalin and sent to the University of Minnesota's Histopathological Core for slide preparation.

Spleens and lungs for FACS analysis were incubated with 37° C. DMEM containing 10% fetal goat serum and crushed with sterile glass stoppers. Homogenates were filtered through a 150-1m nitex mesh (Sefar American, Kansas City, Mo.) and transferred onto 5-mL lymphocyte separation medium (Ficol, Mediatech Inc., Hendon, Va.). The cell suspension was centrifuged for 1 hour and the lymphocyte layer was carefully collected. Cells were serially washed with PBS with 1% bovine serum albumin (BSA) and 0.1% NaN3 (Sigma Chemical) and split for monoclonal antibody staining. Cells were stained with DX5/CD 49a PE and CD 3 FITC for NK cell analysis and CD 8 PerCp and CD4 FITC (Pharminogen, San Diego, Calif.) for T lymphocyte populations. Cells were cold incubated for 30 minutes at 4° C. before a final wash with PSB/BSA/NaN3 and stored under foil at 4° C. until FACS analysis. Splenic and pulmonary lymphocytes collected from experimental mice were analyzed with a FACScalibur (Becton Dickenson, Grenoble, France) and analyzed with Cell Quest Pro Software (Becton Dickenson, San Jose, Calif.). Lymphocyte populations were identified using forward-scatter versus side-scatter profiles and gated for mononuclear lymphocytes. Natural killer cell populations then were identified by DX5/CD 49b$^+$/Cd 3$^-$, $T_H$ and $T_C$ cells by single positive populations based on 10,000 gated events.

Number of tumors, volume, and lymphocyte populations were entered for each mouse at the experimental endpoint to calculate the total mean values for each treatment group. All differences between two groups were determined by Fisher's exact test. Graphs were constructed using Micro-soft Excel (Microsoft, Redmond, Wash.). Statistical tests were performed using StatView software v. 5.0.1 (SAS Institute, Cary, N.C.)

Results

Figure 20:
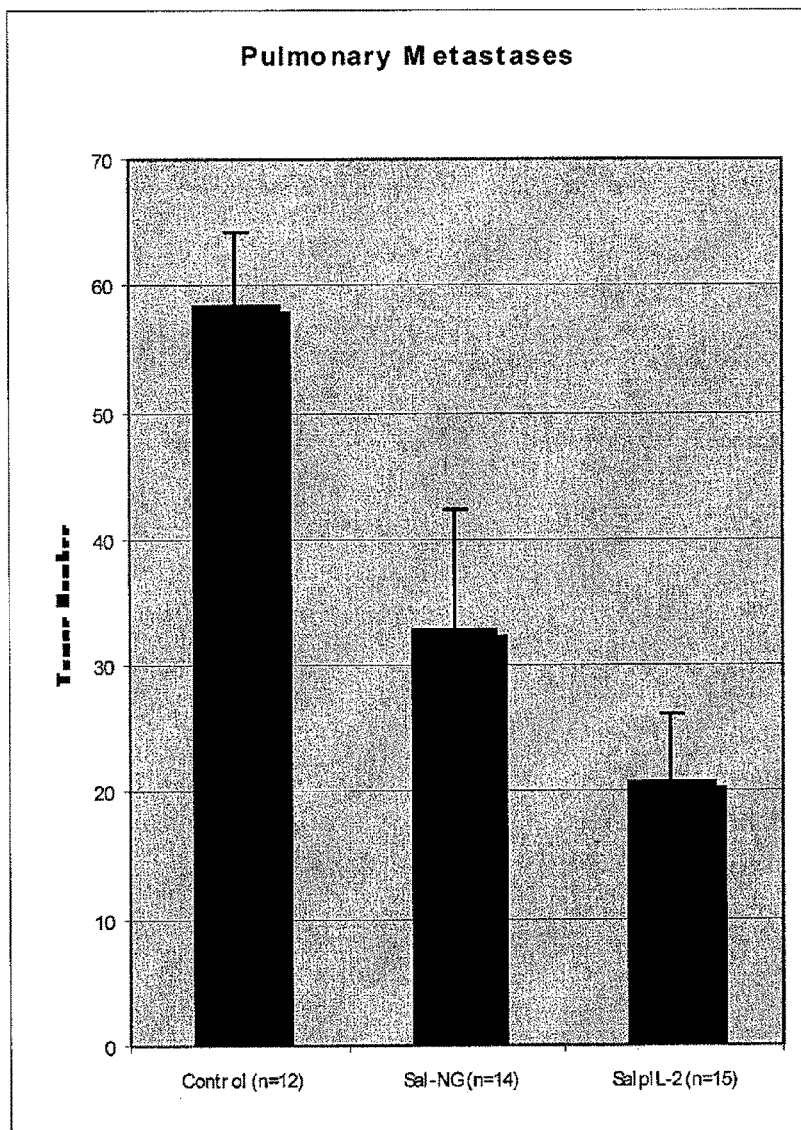
FIG. 20 is a bar graph showing the reduction in tumor number of pulmonary metastases from osteosarcoma in control (saline), *Salmonella typhimurium* χ4550 and *Salmonella typhimurium* χ4550pIL2 with the truncated human IL-2 gene.

Attenuated *S. typhimurium* with and without a gene for truncated human interleukin-2 (SEQ ID NO: 1) had fewer total tumors (20.93 and 33, respectively; p<0.0175 and 0.0006, respectively) compared to saline controls (58.42) (FIG. 20). SalpIL2 reduced (p<0.0037) overall volume of pulmonary metastatic nodules by 78% with respect to saline controls. There was no discernable difference in the reduction of tumor number and volume between the two *Salmonella* treatments. NK cell populations increased (p<0.0163 and p<0.0407, respectively) in Sal-NG- and SalpIL2-treated groups (18.5% and 16.8%, respectively) with respect to saline controls (8.6). Cytotoxic T lymphocyte populations were not noticeably affected by oral administration of Sal-NG and SalpIL2 (p=0.270 and p=0.237) compared to saline controls. T helper cell populations were reduced in the SalpIL2 group (14.3%; p<0.0077) compared to saline controls (20.7%). Local pulmonary lymphocytes collected were elevated in SalpIL2 compared to control and Sal-NG treated animals (p<0.0196 and p<0.0070 respectively). Gross examination of the harvested pulmonary tissues demonstrate the reduction in the mean number of metastatic tumors by SalpIL2 with respect to saline controls. Histological analysis of the tissues treated with SalpIL2 show a decreased invasion of the metastases into the subpleural space and an increase of mononuclear cells in the area.

2. Prevention of Pulmonary Metastases by Administration of SalpIL2 Before Injection with Murine Osteosarcoma Cells.

Seven days before tumor injection, mice were orally gavaged with their respective treatments (n=5), 200 μL Hanks' balanced salt solution for controls or 3×107 CFU of either Sal-NG or SalpIL2. Previously, we established a treatment model for pulmonary metastases to examine the antitumor mechanisms of SalpIL2. In triplicate experiments, animals were anesthetized by intraperitoneal injection of 2:1 xylazine, 20 mg/mL (Phoenix Pharmaceuticals, St Joseph, Mo.), and ketamine, 100 mg/mL (Abbot Laboratories, North Chicago, Ill.). On day 0, animals were prepared and administered 2×105 K7M2 mouse OS cells using well-described techniques. Mice were selected at random from their respective groups for IV tail vein injection. In all experiments, the mice were evaluated for presence of metastases 3 weeks postinjection by euthanasia followed by an intratracheal injection of 1.5 mL of 15% India ink solution via a blunt-ended needle. The stained lungs were carefully resected and rinsed in Feket's solution overnight. Tumors were enumerated and classified by the diameter of the nodules; volume was calculated by $4/3\pi r^3$, assuming the metastases were a sphere. Spleens were aseptically removed and placed in 60×15-mm culture dishes for fluorescent-activated cell sorting (FACS) analysis of splenic lymphocytes.

Splenic Lymphocyte Preparation

Splenic lymphocytes were isolated by mechanically mincing spleens in DMEM containing 10% fetal goat serum. Splenic homogenates were filtered through a 150-μm nitex mesh (Sefar American, Kansas City, Mo.) and separated using density gradient centrifugation in lymphocyte separation medium (Ficol, Mediatech Inc, Hendon, Va.). Cells were serially washed with phosphate buffered saline (PBS) with 1% bovine serum albumin.

Fluorescent-Activated Cell Sorting

Splenic lymphocytes collected from experimental mice were analyzed with a FACSCalibur (Becton Dickenson, Grenoble, France) and analyzed with Cell Quest Pro software (Becton Dickenson, San Jose, Calif.). Lymphocyte populations were identified using forward scatter vs side scatter profiles and gated for mononuclear lymphocytes. Natural killer cell populations then were identified by DX5/CD 49b$^+$/Cd 3$^-$, $T_H$, and TC cells by single positive populations based on 10,000 gated events.

Statistical Analysis

Data for tumor number, volume, and splenic lymphocytes were evaluated by analysis of variance and Fisher's Exact test using Statview statistical analysis software V 5.0.1 (SAS Institute, Cary, N.C.). Graphs and charts were constructed using Microsoft Excel (Microsoft, Redmond, Wash.).

Saline control and SalpI12 treated tissues grossly determined to be representative samples of the mean number of tumors present per group were photographed. Pretreatment with attenuated SalpIL2 and Sal-NG significantly reduced the number of pulmonary metastases (42.87 and 62.69, respectively) with respect to saline controls (183.82; P<0.0001), representing a 77% reduction in tumor. More important, tumor volume was reduced to 49.19 mm$^3$ and 58.13 mm$^3$ by SalpIL2 and Sal-NG as compared to 318.02 mm$^3$ in saline controls (P<0.0001). Furthermore, splenic NK cell populations were increased 396% with SalpIL-2 (11.25%; P<0.0007) and 426% with Sal-NG (12.76%; P<0.0003) compared to saline treated groups (2.84%). CD 8+T lymphocyte populations were unaffected by prophylaxis with SalpIL2 and Sal-NG. However, CD4+ T cells were significantly decreased at the time of animal sacrifice in SalpIL2-treated and Sal-NG-treated groups (11.58 and 11.46, respectively) as compared to saline controls (14.80; P<0.0193 and P<0.0187, respectively).

*Salmonella typhimurium* is a facultative intracellular organism that preferentially tracks to and divides in OS in vitro and reduces tumor burden in a prophylactic model of OS pulmonary metastasis. SalpIL2 was designed to produce a synthetic truncated IL-2, natively a 15-kDa cytokine produced by activated CD4+ T cells as well as other immune cells and is involved in the activation and proliferation of NK cells and T lymphocytes. The IV administration of IL-2 has been associated with severe side effects including fever, fatigue, malaise, and capillary leak syndrome. Numerous attempts have been made to limit the dose-dependent toxicity of IL-2 by altering the route, method, and frequency of dosing. Incorporation of IL-2 into liposomes, single or multilayered lipid vesicles, has resulted in a time-release of soluble effector compounds effecting the drug's toxicity and efficacy.

In one clinical study, a liposomal preparation of IL-2 reduced IL-2 toxicity compared to soluble IL-2. In preclinical trials, liposomal IL-2 was shown to be effective in reducing pulmonary OS metastases in canines. Our laboratory has attempted to establish a local delivery system for IL-2 that may diminish the common side effects associated with IV delivery, by genetically engineering an attenuated strain of *S. typhimurium* to act as a biologic vector for a truncated human IL-2 gene. Other investigators have attempted the use of other strains of attenuated *S. typhimurium* for antitumor therapy, with limited success when given intravenously. Oral administration of SalpIL2 allows the bacteria to follow the natural route of infection and colonize various tissues including the Peyer's patches, liver, lung, and spleen.

We developed our prophylactic models based on the NK cell response after oral administration of SalpIL2. We found the peak NK cell response on day 14 postgavage; thus, tumor cells implanting on day 7 will encounter the highest rate of NK cell proliferation during the infection of SalpIL2. In our prophylactic model, a more dramatic reduction in tumor volume was observed than in our previous treatment model of metastatic OS. Tumor volume was reduced more than 6-fold with SalpIL2 prophylaxis with respect to saline controls. This model represents the subset of patients who do not present with radiologic detectable pulmonary metastases; however, because 80% of patients develop metastatic disease, all patients are thought to have some degree of micrometastases at time of diagnosis. Prophylaxis with SalpIL2 in our model increases systemic NK cells nearly 400% compared to saline-treated animals. Interestingly, we were unable to detect a significant difference between either of the *Salmonella* strains. Previously, we reported that a single oral dose of SalpIL2 significantly increased pulmonary and splenic NK cells in a murine model of OS. In both our treatment and prevention models, we were also unable to detect significant differences in splenic NK or CD 8+ T-cell populations but did find a significant increase of local NK cells in the SalpIL2 group with respect to saline and Sal-NG in the treatment model animals. The presence of an increased local NK cell population suggests functionality of the recombinant IL-2 locally within the pulmonary tissue; however, the fate of the recombinant IL-2 is currently unknown. Additional experiments are necessary to investigate the location of the recombinant IL-2 and whether acute and chronic infections with SalpIL2 produce IL-2 associated toxicities.

Tumors were injected during a peak of an immune response to bacterial infection resulting in a more circulating activated NK cells, prohibiting OS tumor implantation into pulmonary tissue and enhancing tumor surveillance. Immune tumor surveillance is one theory of tumor development; tumors are constantly originating while circulating immune cells, primarily NK cells and cytotoxic T cells provide protection against malignant disease. Depression of the immune system therefore allows tumor cells the ability to escape surveillance and progress to clinical disease. Increasing NK cells may lead to increased interaction between NK and tumor cells, thus inhibiting of cellular invasion and implantation into distant sites. Tumors that do establish as pulmonary metastases are subjected to local inflammatory response to SalpIL2.

Survival for OS has not progressed since the implementation of adjuvant chemotherapy for primary tumors nearly 4 decades ago. Combination therapy has not been shown to be effective in prevention of OS pulmonary metastases. Although the 5-year survival for patients who present without pulmonary metastases has reached 70%, there has been little benefit in the long-term survival of patients who present with pulmonary metastases. Attenuated *S. typhimurium* strains may be a viable biological delivery vector for the treatment and prevention of metastatic OS.

Proposed Theory/Mechanism

The exact mechanism responsible for the improved colorectal cancer response resulting from the administration of *S. typhimurium* χ4550pIL2 concurrently with highly potent antioxidant oils is not yet known. We have shown that *S. typhimurium* χ4550pIL2 alone increases the populations of host effectors cells (NK cells and CD8+ Cytotoxic T cells. Further, it has long been known that both NK cells and $CD8^+$ lymphocytes play an important role in the destruction of tumor cells both in vitro and in vivo.

Oxidative stress is thought to play an important role in the pathogenesis of numerous chronic diseases, such as coronary heart disease and cancer. Although there are many factors in the development of theses diseases, considerable experimental evidence has linked the production of free radicals to biological damage that can provide a basis for the initiation and progression of certain diseases. Free radicals are atoms or molecules that are highly reactive with other cellular structures due to an unpaired electron. Consequently, they are capable of chemically altering nearly all major classes of biomolecules (e.g., lipids, nucleic acids and proteins). Free radicals such as the superoxide anion, the hydroxyl radical and singlet oxygen can be produced in vivo by factors such as dietary imbalances, tobacco smoke, pollutants or from sources such as lipid peroxidation, inflammation and biochemical reactions. They are capable of damaging DNA, inhibiting its repair and amplifying viral and oncogene expression. Interestingly, free radicals are also generated by cells of the immune system to destroy invading organisms. However, the presence of these strong oxidants places additional stress on the immune system, which can result in a diminished response against invaders. Furthermore, the long-term presence of these oxidizing species will eventually be detrimental to the human body.

Humans and other aerobic organisms have evolved a variety of mechanisms to protect themselves from the deleterious effects of free radicals. These defense mechanisms protect against free radical damage either directly or indirectly. The defense mechanisms include enzymes such as catalase and superoxide dismutases and repair enzymes such as DNA glycosylases. Water and lipid-soluble antioxidants such as ascorbate (vitamin C), α-tocopherol (vitamin E) and beta carotene also act to eliminate free radicals. These antioxidants help shield DNA from the deleterious effects of oxidative damage by absorbing unstable oxygen molecules.

A number of sources indicate a relationship between diet and cancer incidence in humans. The geographic distribution of types of cancer, the changing cancer patters and data from experimental animal studies all indicate that diet and nutrition are important factors in the control and prevention of human cancers. The potential importance of diet in cancer prevention is also noted by the suspected causes of some cancers. Most cancers (an estimated 80% to 90%) have environmental causes and are therefore potentially preventable. Much controversy surrounds the actual percent of cancers associated with dietary factors, but it has been estimated that in men 30% to 40% of all cancers are in some way related to diet. In women, it is believed that 60% of all cancers are related to diet. Another study estimates that 35% of cancer is diet related. Regardless of the exact numbers, these are impressive percentages.

Presumably, pathology due to oxidative stress results when the generation of free radicals exceeds the cell's capacity to protect or repair itself. Therefore, if oxidative damage is an important etiologic factor in the pathogenesis of diseases such as cancer, then it follows that antioxidants, which act to reduce oxidative stress, may play a role in the prevention or treatment of these diseases. The accumulation and growth of free radicals in tissues is often found in association with suppressed immune function, infections such as HPV and HIV, cancer and heart disease. In fact damage to heart blood vessels and the incidence of coronary heart disease has been shown to be reduced with increased dietary antioxidant intake. The protective effects of topical antioxidants (vitamin A derivatives such as retinoic acids) against proliferative dermatological diseases as well as photo-aging have been well documented. Many studies continue to demonstrate below normal antioxidant tissue and blood plasma levels in women with HPV and other cervical neoplasms, while high levels provide protection against their initiation and progression.

Like the B vitamins, the beneficial effects of antioxidants are most notable when combined with one another. In fact, diets high in antioxidants (e.g., the traditional Greek Mediterranean diet) have been shown to be protective against cancer and various diseases. It is believed that antioxidants alter cancer incidence and growth by acting as anticarcinogens. Nutritional anticarcinogens function by (a) inhibition of tumor initiation via alteration of cellular metabolism, (b) picking up active forms of carcinogens and preventing them from reaching target sites, (c) alteration of the body's defense systems, (d) inhibition of cancer progression once it has been initiated by the alteration of cell differentiation, and (e) prevention of gene activation and cellular proliferation by tumor promoters.

It is also known that in individuals, and in entire populations, showing the lowest rates of colorectal cancer occur when diets rich in fruits and vegetables are consumed. One possible mechanism for this phenomenon is that fruits and vegetables contain anticarcinogens, such as antioxidants, that prevent the development of colorectal tumors. It is believed that antioxidants may inhibit the process of lipid peroxidation and reduce the formation of mutagenic peroxidation products in the colon. It is hypothesized that specific receptor populations for NK cells and CD8+ Cytotoxic T cells are increased by the administration of an effective amount of *S. typhimurium* χ4550pIL2 together with highly potent antioxidant oils, such as black raspberry oil. An alternative hypothesis suggests that the administration of an effective amount of *S. typhimurium* χ4550pIL2 together with highly potent antioxidant oils, such as black raspberry oil somehow sends a signal to the cellular genetic machinery to increase the number of receptors and/or cell populations themselves.

It is believed that the administration of *S. typhimurium* χ4550pIL2 concurrently with highly potent antioxidant oils will also be effective in treating infectious disease, other cancerous tumors, slowing the ageing process and treating other immuno-compromised states, including HIV infections. An additional use of the present invention would be administering it to cancer patients between periods of chemotherapy and/or radiation treatments. It is further believed that the composition containing *S. typhimurium* χ4550pIL2 concurrently with highly potent antioxidant oils will also be effective as a preventive treatment when used in patients with high risk factors for colon cancer such as family or behavioral history.

Use

Prior to the oral delivery of the *S. typhimurium* χ4550pIL2 and anti-oxidant oil alkalization of the patient's stomach is necessary to neutralize gastric acid to prevent the acid induced destruction of the *S. typhimurium* χ4550pIL2. This is accomplished by orally administering 30 ml of Bicitra® 15 minutes prior to administering the *S. typhimurium* χ4550pIL2 with anti-oxidant oil. A dose containing approximately $10^6$ to $10^8$ *S. typhimurium* χ4550pIL2 is administered to a human patient once, at the initiation of treatment. Approximately one-half teaspoon of cold pressed black raspberry oil is administered to the patient twice a day, throughout the treatment period. As treatment continues, the dosage of each may be escalated or altered as indicated.

While the above description of use of the present invention is specifically directed to human beings, it is also speculated that the present invention would also be effective in treating agricultural (e.g., cattle, swine, sheep, horses, domesticated fowl) and companion (dogs, cats, birds) animals.

Although the present invention has been described in considerable detail with reference to certain preferred versions thereof, other versions are also possible. Therefore, the spirit and scope of the appended claims should not be limited to the description of the preferred versions contained herein.

Proposed Human Clinical Trial (Phase 1)

The following has been submitted to the U.S. Department of Health and Human Services, Food and Drug Administration, in an Investigational New Drug Application (IND) for "*Salmonella typhimurium* Expressing IL-2 Gene, Attentuated; Administered Orally." Clinical hold has been removed and permission has been granted to proceed with the study.

SCHEMA

Enrollment of patients with solid tumors metastic to the liver
No other effective therapy available 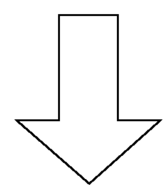 Oral Salmonella, single dose
Monthly tumor assessments
Weekly stool cultures Dose Escalation Schedule

| Dose Level | Dose of Salmonella (number) |
|---|---|
| Level 1 | $10^5$ |
| Level 2 | $10^6$ |
| Level 3 | $10^7$ |
| Level 4 | $10^8$ |
| Level 5 | $10^9$ |

1. Objectives 1.1 Assess the safety of oral administration of an attenuated strain of *salmonella typhimurium* expressing IL-2 in patients with cancer metastatic to the liver.

1.2 Assess the in vivo production of IL-2 and its effect on immune function.

1.3 Assess the length of colonization and excretion with the modified bacterium.

2. Background 2.1 Rationale

IL-2, a 15-kilodalton cytokine, is produced by activated CD4+T cells. It promotes lymphocyte proliferation and enhances the cytolytic function of T cells and NK cells.3,4 The ability of IL-2 to facilitate cytolytic activity in lymphocytes and to induce the lymphokine-activated killer (LAK)

phenomenon with subsequent malignant cell destruction has resulted in decades of studies of IL-2-based immunotherapy.[5,6] With and without adoptively transferred IL-2 activated cells, IL-2 has been effective in murine tumor models and in a limited number of human patients with malignancies, including renal cell carcinoma and melanoma.[7-9] However, high doses of IL-2 have resulted in severe toxicity in many patients, thereby limiting its use. Major toxicities associated with high-dose IL-2 administration include malaise, fever, anasarca, jaundice, renal dysfunction, and capillary leak syndrome.[10,11]

Investigators have attempted to diminish the adverse effects of systemically administered IL-2 by altering the dose, schedule, route, and rate of infusion; however, the toxic effects of IL-2 therapy have persisted to some degree.[3-11] Local delivery of IL-2 may produce less toxicity.[4] IL-2 liposomes reportedly modify the pulmonary toxicity of IL-2 by altering the absorption and distribution of the entrapped drug.[11] Thus, local effects achieved with a depot preparation of IL-2 improved the therapeutic index.

*Salmonella* are gram-negative facultative intracellular organisms that can cause a wide spectrum of disease in both humans and animals. After oral administration, *Salmonella* penetrate into the Peyer's patches of the intestine, where they can be phagocytosed by the resident macrophages and then carried through the reticular endothelial system before finding a safe site within the liver and spleen.[12] In addition, *Salmonella* may be disseminated systemically within the local macrophages, which subsequently induce humoral and cellular immune responses.[13] An alternatative mechanism of invasion has been described where *Salmonella* are engulfed by dendritic cells at the mucosal surface and then transported from the gastrointestinal tract to the bloodstream by macrophages.[14] Unlike other invasive bacteria, *Salmonella* can reside and divide within macrophages, the antigen-presenting cell. Peptides resulting from bacterial degradation are packaged, bound to the major histocompatibility complex (MHC) class II molecules, and presented to CD4+ T cells. In addition, antigen-specific cytotoxic CD8+ T cells against proteins expressed by the *Salmonella* carriers can also be stimulated. This cytotoxic response appears to take place through an alternative MHC class I processing pathway.[14]

Capitalizing on the unique ability of this organism to invade host tissue and trigger a local as well as systemic immune response, researchers theorized that attenuation of *Salmonella* could preserve their abilities of invasion and immune stimulation while ameliorating their deleterious effects.[15] Attenuation of *Salmonella* has been achieved by several methods. In human trials, chemical attenuation of *Salmonella typhi* conferred both local and systemic humoral and cellular immunity with a significant but incomplete protection against typhoid fever.[16] Subsequently, several attenuated strains of both *S. typhi* and *S. typhimurium* were developed by deleting 2 genes encoding essential enzymes in the biosynthesis of aromatic compounds (aroA) and adenine (purA). These attenuated bacteria were well-tolerated but not as immunogenic, leading to the developments of these auxotrophic strains. Although auxotrophic strains were more immunogenic, transient bacteremia was seen in human volunteers.[15] Curtiss et al. were primarily responsible for developing attenuated strains of *Salmonella* that lack the genes encoding the adenylate cyclase (cya) and cyclic adenylate cyclase (crp) receptors. These bacteria were found to be highly immunogenic and safe in human volunteers, with 80% to 100% of whom demonstrated seroconversion to bacterial antigens.[17-19]

Attenuated *Salmonella* species are effective vaccine carriers. Examples include attenuated *S. typhimurium* vaccines for murine listeriosis and the human papillomavirus type 16.[20] In addition, *S. typhimurium* species appear to have the unique propensity to track to tumor cells, and clinical trials have been initiated using an intravenous injection of an attenuated form of *S. typhimurium*, lacking aroC, in human patients with widespread malignancies.[21,22] In animal studies, attenuated *Salmonella* as anti-cancer agents have been primarily used in mouse models, using various routes of delivery: oral or injected, either intratumoral or intravenous. One study focused on the antitumor potential in mice with intravenous injection of attenuated *Salmonella* to treat a multitude of tumor types that were subcutaneously implanted: *Salmonella* accumulated in tumors more readily than in the normal liver reservoir; despite partial inhibition of tumor growth, ultimately progressive growth was observed for all tumor types.[24]

Characterization of the *Salmonella* pathogenicity island (SPI) genes revealed that one cluster, the SPI-1 genes, promote invasion from the intestine, while another cluster, the SPI-2 genes, support systemic survival within macrophages and other cells. In a subcutaneous melanoma model, SPI-2 genes appeared to be essential for tumor growth suppression.[23]

There have been numerous studies examining the immune effectiveness of *Salmonella* vaccines for various entities in human volunteers. The results have been mixed—some studies documented an immune response to a particular foreign antigen, while others did not. Most researchers speculate that this mixed response results from the method of attenuation for the particular strain of *Salmonella* used, the type of adjuvant used, the foreign protein being expressed, or the route of administration of the *Salmonella*. Clinical experience with *Salmonella* to treat malignancies has been sparse. To date, 2 clinical studies have used *Salmonella* for cancer treatment.[21,22] The first involved patients with metastatic malignant melanoma and metastatic renal cell carcinoma. These patients received intravenous attenuated *Salmonella* on a dose escalation schedule of $10^6$ to $10^9$ bacteria administered over a 4-hour interval. They all appeared to tolerate intravenous infusion of the bacteria, and some of them had tumor colonization by the bacteria> But, only 1 patient demonstrated a complete response and was free of tumor 3 months after infusion. The remaining patients all had progression of disease. Interestingly, most patients demonstrated a dose-related increase of the proinflammatory cytokines interleukin-1 (IL-1), tumor necrosis factor-alpha (TNF-α), interleukin-6 (IL-6), and interleukin-12 (IL-12). In addition, most of these patients also developed strain-specific IgG and IgM antibodies.

In contrast to intravenously administered *Salmonella*, the second trial used an intratumoral injection of attenuated *Salmonella* expressing the *Escherichia coli* cytosine deaminase gene with concomitantly administered 5-fluorocytosine.[32] This intratumoral study included 3 patients with various tumor types. All 3 converted 5-fluorocytosine to 5-fluorouracil, yet disease progression persisted; 1 patient had to be removed from the study because of the development of significant toxicities.

2.2 Study Agent: Attenuated *Salmonella typhimurium* Containing the Gene for Human IL-2 (*Salmonella* χ4550(pIL-2))

In contrast to the *Salmonella* used in these 2 clinical trials, we propose ORAL administration of the bacteria. The use of live attenuated *Salmonella* as IL-2 carriers has been investigated for several reasons. First, *Salmonella* naturally colonizes the gut-associated lymphoid tissue (GALT), liver, and spleen.[12] Second, colonization of the liver and spleen initiates a generalized cellular immune response against the bacteria and can also induce a carrier state. In addition, attenuated *Salmonella* have been shown to preferentially invade various subcutaneous tumors more readily than liver tissue, at tumor-to-liver ratios ranging from 250:1 to 9000:1.[25]

We have used the χ4550 strain of *S. typhimurium* as our parental strain. It lacks the enzyme aspartate semialdehyde dehydrogenase (asd), which is contained in the pYA292 plasmid. Bacteria that lack asd cannot make diaminopimelic acid (DAP), an essential component of the bacterial cell wall, and cannot survive unless they carry a plasmid with the asd gene or unless DAP is provided in the growth media. We have also modified the pYA292 plasmid, which contains the asd gene, and is therefore capable of rescuing χ4550 *S. typhimurium*, by incorporating the gene for human IL-2 (pIL2). Thus, we have 2 strains of attenuated *S. typhimurium* that have been transformed either with the empty pYA292 plasmid (hereafter referred to as attenuated *Salmonella* lacking the IL-2 gene [*Salmonella*-no-IL2]), or attenuated *Salmonella* with the pIL2 plasmid (hereafter referred to as: attenuated *Salmonella* containing the IL-2 gene [*Salmonella*-IL2]). Because the loss of the IL-2-containing pYA292 plasmid (pIL2) would also result in the loss of the plasmid-encoded asd, we have achieved stable expression of human IL-2.

We have submitted an Investigational New Drug (ND) application to the U.S. Food and Drug Administration (FDA) and are in the process of responding to the request for more information. If our IND is approved, we plan to conduct a Phase I clinical trial using ORALLY ADMINISTERED_attenuated *Salmonella*-IL2 for patients with unresectable hepatic metastases from any gastrointestinal malignancy.

Preliminary Studies

Our research laboratory has extensive experience with attenuated *Salmonella*-IL2 for unresectable adenocarcinomatous liver metastases, osteogenic sarcomatous lung metastases, and primary neuroblastoma.[26-31] A brief summary of our findings follows:

IL-2 produced by *Salmonella*-IL2 is biologically active. We studied murine splenocyte NK function as an indicator of in vivo IL-2 biologic activity. We conducted duplicate experiments in which C57BL/6 mice were randomly divided into 3 groups. We grew suspensions of *Salmonella*-IL2, which exhibited the high IL-2 production to $10^{10}$ CFU/ml; then gavage fed $10^9$ CFU in 0.25 mL to the first group. We used a suspension of $10^9$ CFU in 0.25 mL of the attenuated *Salmonella*-no-IL2 as a negative control to gavage the second group, and saline to gavage the third group. On days 3 and 7 after gavage, we isolated splenic mononuclear cells using a Ficoll density sedimentation gradient. Interface mononuclear cells were used as effector cells in a 4-hour $^{51}$Cr release cytotoxicity assay against NK-sensitive YAC-1 lymphoma cells. We found that the splenocytes of mice gavage-fed *Salmonella*-IL2 had significantly increased splenocyte NK activity on days 3 and 7 after gavage, as compared with mice gavage-fed either saline or *Salmonella*-no-IL2. Our findings on day 3 (Table 1) and day 7 (data not shown) did not differ significantly and strongly suggest that the IL-2 produced by *Salmonella*-IL2 was biologically active.

TABLE 1

| Day 3 Effectors | |
| --- | --- |
| Murine Splenocytes | % Cytotoxicity |
| Control | 15.0% ± 6.3 |
| *Salmonella*-no-IL2 | 17.3% ± 4.7 |
| *Salmonella*-IL2 | 30.5% ± 6.7 |

Attenuated *Salmonella*-IL2 Suppresses In Vivo Tumor Metastases.

Figure 21:
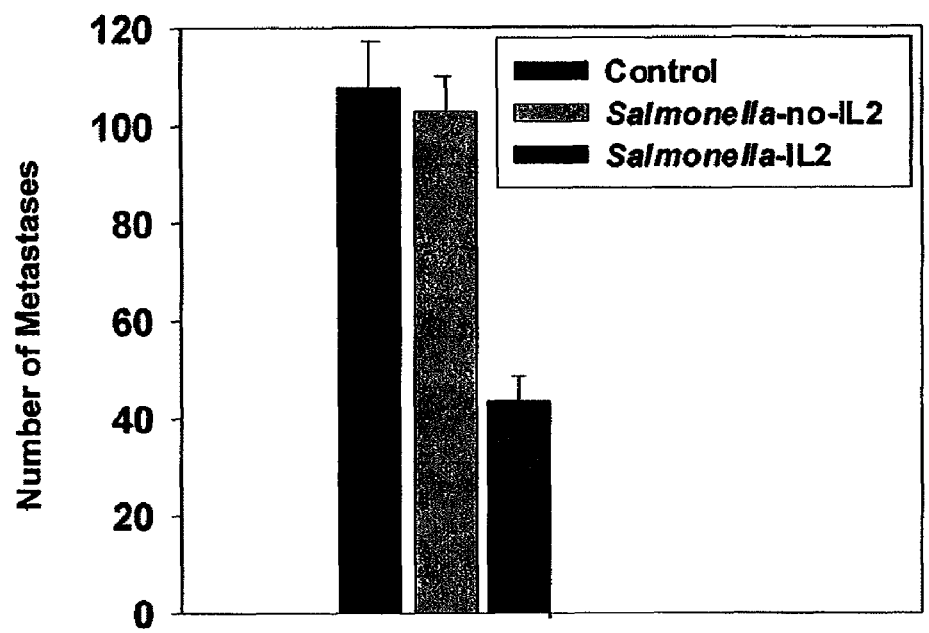
FIG. 21 is a bar graph showing the reduction in number of hepatic metastases in mice orally administered *Salmonella*-IL2 vs. saline (control) or SaS *Salmonella*-no-IL2.
Figure 22:
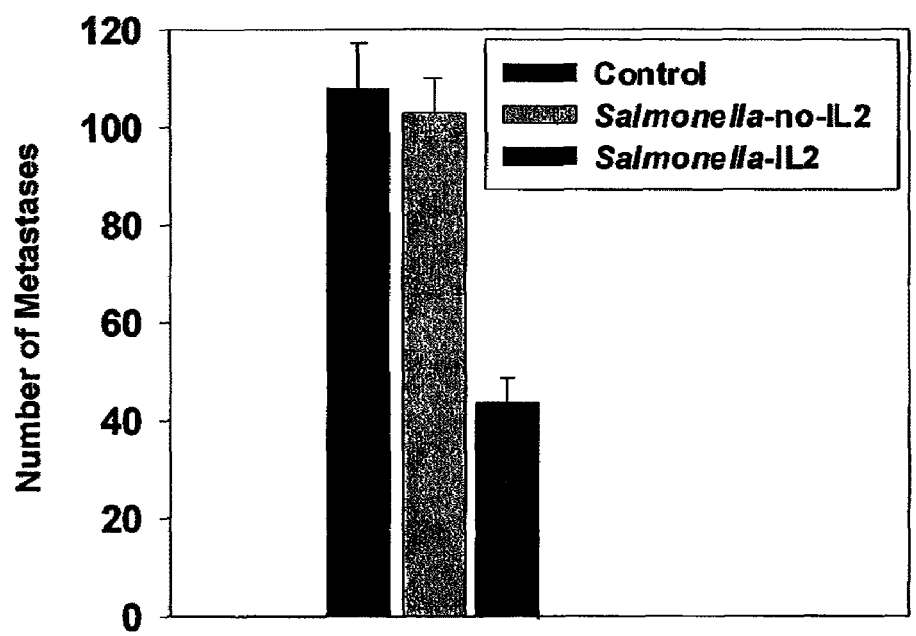
FIG. 22 is a bar graph showing the reduction of liver metastases in mice treated with *Salmonella*-IL2 where NK and CD8+ cell populations were depleted.

We evaluated the in vivo antitumor efficacy of *Salmonella*-IL2, using murine MCA-38 adenocarcinoma hepatic metastases generated in C57BL/6 mice. Our experimental design was based on the Rosenberg model of murine adenocarcinomatous liver metastases; briefly, it consists of performing an intrasplenic injection of $2\times10^5$ MCA-38 adenocarcinomatous cells that ultimately result in liver metastases.[24] We divided mice into 3 groups, 3 days after tumor inoculation and gavage-fed them a single oral dose of (1) saline, (2) *Salmonella*-no-IL2, or (3) *Salmonella*-IL2. We enumerated surface metastatic deposits 14 days after tumor inoculation. As shown in FIG. 21, we found a significant reduction in the number of liver metastases in the *Salmonella*-IL2 group, as compared with either the control group or the *Salmonella*-no-IL2 group.

NK Cells and CD8$^+$T Cells are the Major Mediators of the Antitumor Response Elicited by *Salmonella*-IL2.

Our observation that *Salmonella*-no-IL2 did not demonstrate an antitumor effect led us to surmise that cytokines produced by the host in response to *Salmonella* colonization alone does not appear to cause these antitumor effects. We sought to determine which host effector cell population was responsible for the antitumor effect seen with *Salmonella*-IL2. Since IL-2 directly enhances antitumor cytolytic function of NK cells, macrophages, and T cells and promotes lymphocyte proliferation, any of these cellular mechanisms could contribute to the significant reduction of liver metastases seen with *Salmonella*-IL2. We used our standardized treatment model of liver metastases in 4 cohorts of mice (1) untreated control mice gavage-fed saline, (2) untreated control mice gavage-fed saline and depleted of a particular host effector cell population, (3) treated mice gavage-fed *Salmonella*-IL2, and (4) treated mice gavage-fed *Salmonella*-IL2 and depleted of a particular host effector cell population. Specific host effector cell populations that were depleted included NK cells, CD8+ cells, CD4+ cells, and liver Kupffer cells. We found that the number of liver metastases was reduced in mice that had been treated with *Salmonella*-IL2, as compared with control mice treated with saline. This effect was abrogated in mice in which either the NK or the CD8+ effector cells were depleted, but not in mice in which either the CD4+ effector cells or liver Kupffer cells were depleted (FIG. 2). This difference is not surprising because both NK cells and CD8+ cells are known to generate direct tumor destruction. IL-2 markedly potentiates NK cell cytolytic activity against tumor cell targets through the secretion of cytolytic molecules such as perforin and the granzymes. NK cells kill their targets in an MHC unrestricted fashion, while CD8+ cells require the expression of MHC class I by the tumor for effective recognition and killing to take place. CD4+ cells are usually not cytolytic, but have been shown to kill MHC class II tumor targets. Because the tumor used in these studies, MCA-38, does not express MHC class II, it is not surprising that depletion of the CD4+ cell subset did not affect the antitumor response elicited by *Salmonella*-IL2.

In addition to NK, CD8+, and CD4+ lymphoid cells, we studied the role of the liver Kupffer cells on the antitumor response elicited by *Salmonella*-IL2. *Salmonella* species are facultative intracellular parasites that mainly localize in Kupffer cells and multiply intracellularly. Murine Kupffer cells respond expansively to exogenously administered IL-2 and participate in the induction of antigen-specific immune responses. We did not find that the depletion of Kupffer cells adversely affected the antitumor response elicited by *Salmonella*-IL2.

Attenuated *Salmonella* invades different tumor cell lines. The unique ability of attenuated *Salmonella* to maintain immunogenicity after having lost the ability to cause disease has led to more than a decade of study of this organism's therapeutic potential in cancer patients. *Salmonella* can grow under anaerobic and aerobic conditions, and can survive within epithelial cells as well as macrophages. The precise mechanism of invasion and the antitumor effect seen with attenuated *Salmonella* in cancer treatment is poorly understood. However, attenuated *Salmonella* administered intravenously seem to preferentially accumulate within subcutaneously placed tumors, as compared with its normal host reservoir, the liver. Other researchers have replicated these findings and have shown that attenuated *Salmonella* can halt the growth of subcutaneous tumors. However, how *Salmonella* accumulate within tumors is not entirely clear. We investigated the ability of our attenuated *Salmonella*-IL2 to invade at 5-, 10-, and 15-minute intervals, or to multiply within different cancer cell lines: rat hepatocellular carcinoma (Morris7777, hepatoma), mouse neuroblastoma (N2a, neuroblastoma), mouse methylcholanthrene-induced colon carcinoma (MCA-38, colon cancer), and mouse osteosarcoma (K7M2, osteosarcoma). We used murine hepatocytes (liver) as a positive control and saline as a negative control (control).

Figure 23:
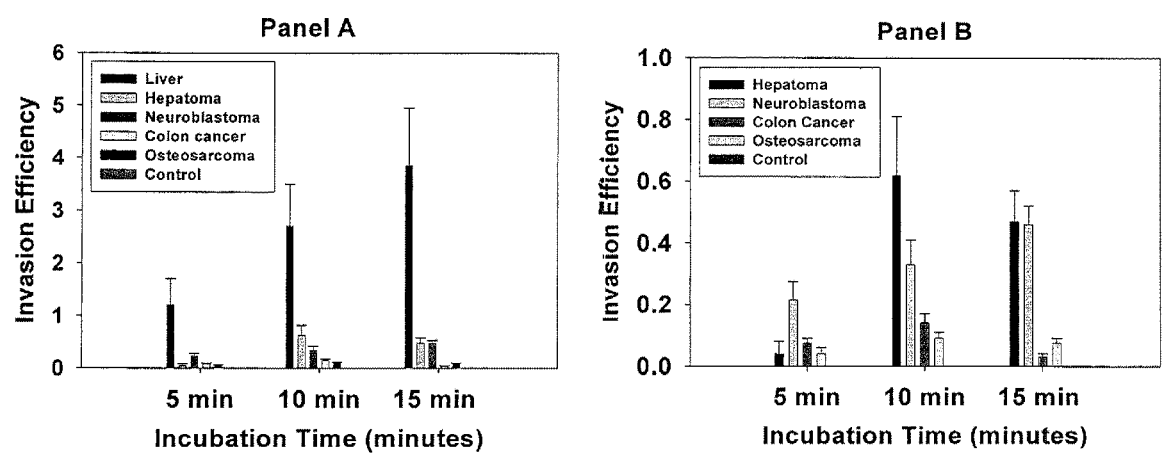
FIG. 23 is a bar graph showing that the invasion efficiency of *Salmonella*-IL2 is greatest in hepatocytes, but *Salmonella*-IL2 also invades various tumor cell lines.

We found that attenuated *Salmonella*-no-IL2 and *Salmonella*-IL2 displayed equal invasion efficiencies (percentage of intracellular *Salmonella* recovered from inocula) into hepatocytes and all cancer cell lines (data not shown). FIG. 23, Panel A shows that the ability of *Salmonella*-M2 to invade cultured hepatocytes (liver) was much higher than that of any cancer cell line at all incubation times ($p<0.05$), displaying a stepwise linear increase in bacterial invasion with increasing bacterial exposure times. Posthoc analysis of the *Salmonella*-IL2 invasion among cancer cell lines revealed a divergence in invasion efficiency between neuroblastoma and hepatocellular carcinoma as compared with osteosarcoma or human colon cancer cell lines. FIG. 23, Panel B is an expanded portion of FIG. 23, Panel A excluding the data from the murine hepatocyte invasion.

Figure 24:
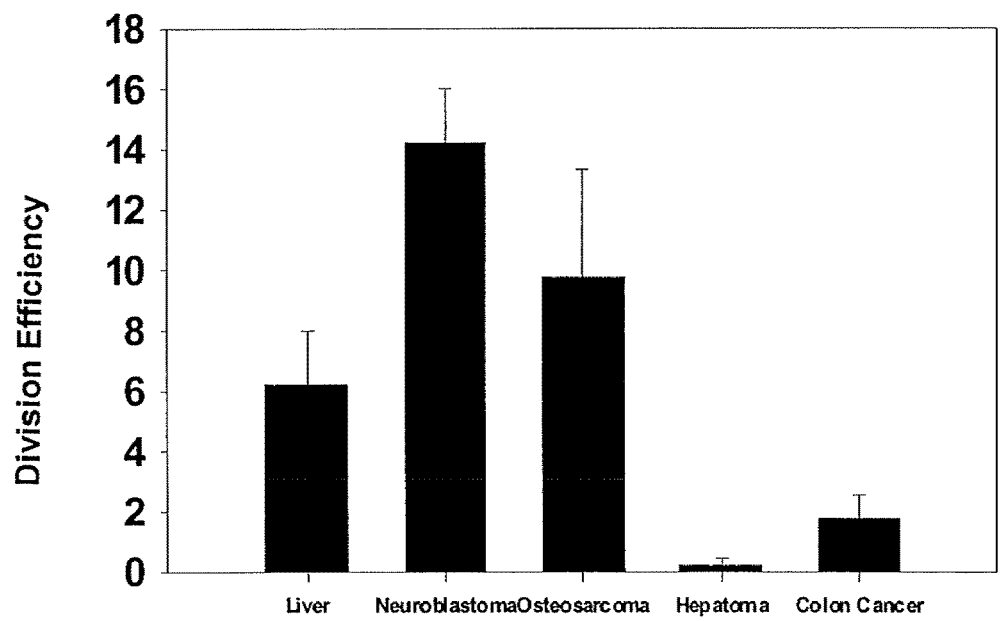
FIG. 24 is a bar graph showing that the division efficiency of *Salmonella*-IL2 is greatest within neuroblastoma and osteosarcoma tumor cell lines over a 24-hour period compared with hepatoma and colon cancer cell lines.

Attenuated *Salmonella* replicates intracellularly in different tumor cell lines. Once we observed that attenuated *Salmonella* differentially invades tumor cells, we were curious to determine any differences in intracellular division by this organism within the different tumor cell lines themselves. We defined the division efficiency as a measure of intracellular proliferation, infected confluent suspensions of tumor cells with *Salmonella*-pIL2, and assessed intracellular growth of the bacteria after 24 hours. Again, we found no difference between the division efficiency of *Salmonella*-no-IL2 and *Salmonella*-IL2. FIG. 24 shows that *Salmonella*-IL2 replicates with greater efficiency within neuroblastoma and osteosarcoma cancer cells, as compared with liver, hepatoma, or colon cancer cells. Overnight incubation revealed greater intracellular division of *Salmonella*-IL2 in neuroblastoma cells as compared with hepatocytes (liver), hepatoma, or colon cancer cells. The intracellular division of *Salmonella*-IL2 within osteosarcoma was significantly greater, as compared with hepatoma or colon cancer cells. Therefore, not only do attenuated *Salmonella*-no-IL2 and *Salmonella*-IL2 display an enhanced invasion into neuroblastoma and osteosarcoma (as compared with the other malignant cells) but also, the intracellular proliferation of the bacteria is augmented as well.

The invasion of wild-type *S. typhimurium* into enterocytes is a well-defined process. We previously demonstrated that attenuated *Salmonella*-IL2 invasion into the enterocyte cell lines CaCo-2 and HT-29 cells is significantly diminished as compared to its wild-type counterpart. This finding partially accounts for its lower virulence and near absence of *Salmonella*-associated gastroenteritis. Our attenuated *Salmonella*-IL2 invasion into malignant cell subsets is not as effective as its invasion into hepatocytes, the normal colonization site for this organism. Furthermore, when we analyzed the invasiveness of *Salmonella*-IL2, we found a difference between wild-type *S. typhimurium* and attenuated *Salmonella*-IL2. Differences in the expression of cell surface proteins may account for this observation. Wild-type *S. typhimurium* invasion into enterocytes depends on activation of plasma membrane-associated GTP-binding proteins, such as CDC42 and/or Rac1. The binding of *Salmonella* to these proteins catalyzes a cascade of intracellular signaling that results in membrane ruffling and macropinocytosis of bacteria. Therefore, differences in expression of Rac1 and CDC42 could explain the variability of *S. typhimurium* invasion into hepatocytes and malignant cell subsets.

Invasive *Salmonella*-IL2 invasion of neuroblastoma cells is visualized in vivo. We and others have shown that *Salmonella* track to tumor tissue in vitro, and we also devised a method to directly visualize *Salmonella*-IL2 invasion of neuroblastoma cells in vivo. We modified our existing attenuated *Salmonella* strains, *Salmonella*-no-IL2 and *Salmonella*-IL2, by transforming these bacteria with a commercially available plasmid containing the green fluorescent protein. Transformants were selected by using the ampicillin resistance conferred by the GFP plasmid. The GFP-transformed bacteria were used in our standard retroperitoneal neuroblastoma model: 14 days after retroperitoneal injection of N2a cells, we gavage-fed mice $10^8$ CFU of either *Salmonella*-no-IL2-GFP or *Salmonella*-IL2-GFP. Then, 1 week later, we sacrificed the mice, enumerated their tumors, prepared frozen tissue sections from the tumors, and examined the sections under the fluorescent microscope. Only *Salmonella*-no-IL2-GFP or *Salmonella*-IL2-GFP constructs grew on agar plates containing ampicillin. We examined colonies on the ampicillin-containing plates under the fluorescent microscope and found the expected green fluorescence at 488 nm. We found intracellular bacteria in the tissue sectioned from neuroblastoma extracted from mice treated with *Salmonella*-no-IL2-GFP or *Salmonella*-IL2-GFP and excited at 488 nm. Intracellular *Salmonella*-IL2-GFP bacteria fluoresce more brightly than the surrounding tissue. We also found small numbers of fluorescent bacteria in the liver, spleen, and lungs. Tissue sections examined from mice gavage-fed with non-GFP-transformed *Salmonella*-no-IL2 and *Salmonella*-IL2 demonstrated no fluorescence when excited at 488 nm.

Figure 26:
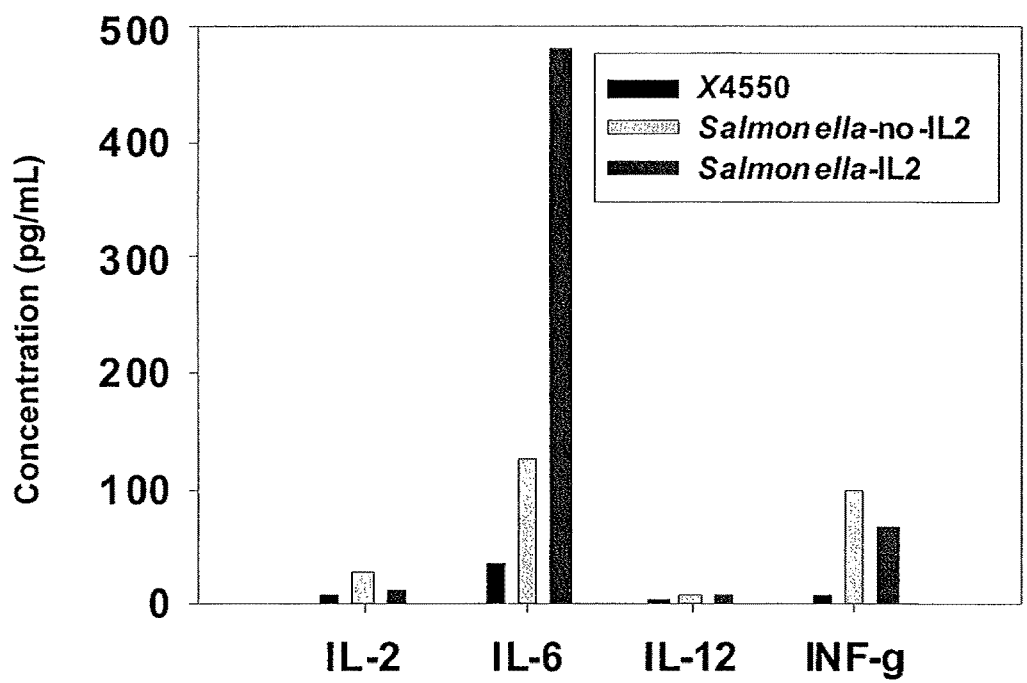
FIG. 26 is a bar graph showing serum cytokines at day 14 after gavage treatment in retroperitoneal neuroblastoma.
Figure 25:
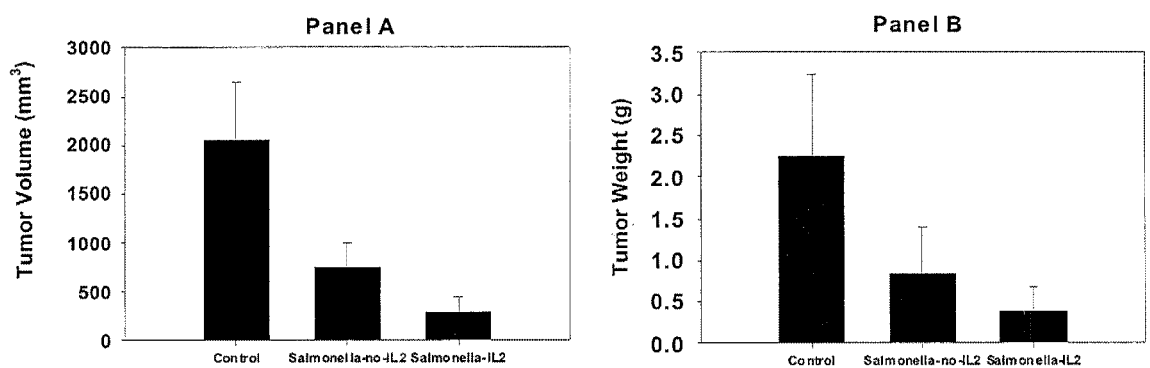
FIG. 25 is a bar graph showing that the tumor volume (Panel A) and weight (Panel B) of retroperitoneal neuroblastoma in animals are reduced in mice treated with *Salmonella*-no-IL2 and *Salmonella*-IL2.

One oral dose of attenuated *Salmonella* nearly eliminates neuroblastoma. Given our finding of improved attenuated *Salmonella* invasion and division efficiency in neuroblastoma cells, we again used our standard vivo murine model of retroperitoneal neuroblastoma and investigated the antitumor effect of attenuated *Salmonella*. We found that treatment with *Salmonella*-no-IL2 and *Salmonella*-IL2 resulted in a significant reduction in both tumor volume (FIG. 25, Panel A) and tumor weight (FIG. 25, Panel B), as compared with saline controls. Tumor volume is calculated assuming tumor shape as a sphere ($4/3\ \pi r^3$). When comparing reductions between mice treated with *Salmonella*-no-IL2 and *Salmonella*-IL2, we found statistically significant decreases in tumor volume and in tumor weight. Cytokines proliferate in response to attenuated *Salmonella*. In an effort to look more closely at the mechanisms by which attenuated *Salmonella* affect neuroblastoma tumors, we evaluated, in our in vivo retroperitoneal neuroblastoma model, the systemic cytokines, IL-2, IL-6, IL-12, and interferon-gamma (IFN-γ) of cohorts of mice 14 days after treatment with saline (controls), with *Salmonella*-no-IL2, or with *Salmonella*-IL2. FIG. 26 shows a dramatic increase in the amount of systemic IL-6 in mice treated with *Salmonella*-IL2. IL-6 is a pleiotropic cytokine with a variety of immunomodulatory roles, including the activation of cytotoxic T cells and NK cells. We previously showed IL-6 to be important in reducing the tumor burden in our model of liver metastases of colon cancer. We found no upregulation of systemic IL-2, suggesting that the IL-2 produced by *Salmonella*-IL2 exerts its effect locally.

Safety of Study Agent

Each of the family of attenuated strains, including our own χ4550 strain as described above, given orally to mice at doses up to $10^9$ organisms failed to cause any mortality or morbidity. The genes for cya and crp are widely separated on the *salmonella* genome making reversion to wild-type for both genes extremely unlikely. When parent strains were grown to late log phase and plated on minimal agar medium with various carbohydrates that should not support growth, occasional mutants were seen with the single deletion (cya−) strain χ4032, and very rare mutants with the double deletion (cya−/crp−) strain χ4064. When these apparent mutants were re-administered to mice they remained avirulent. In humans, a cya−/crp− attenuated *salmonella* (derived from a different virulent strain) using the asd− balanced lethal vector system (as in χ4550) showed little to no virulence in 22 human volunteers.[28] Over the course of our experiments described above, the study agent has been administered to over 4000 mice without apparent adverse effect. As the study agent has never been administered to humans, this study will provide for first data on human safety.

2.3 Study Disease: Carcinoma Metastatic to Liver

It is estimated that 130,000 new cases of colorectal carcinoma occur in North America per year. Of these patients, it is expected that 40 to 50 percent will experience a recurrence within 5 years. Furthermore, it is known that 75 to 80 percent of patients with a recurrence would have the liver as one of the involved sites for metastasis with 15 to 20 percent having the liver as the only site of failure.[2] Surgical excision of the hepatic metastases is the only potential for cure in these patients. Unfortunately, when a diagnosis of hepatic metastases is established, the majority of these patients have unresectable disease.[1,2]

Unresectable metastatic carcinoma of the liver—regardless of the primary site—continues to have a very poor prognosis despite recent advances with chemotherapeutic and radiotherapeutic strategies, chemoembolization, radiofrequency ablation, and cryotherapy.[7] Thus, a large body of research continues to be conducted, searching for an effective means to combat unresectable metastatic carcinoma of the liver.

---

What is claimed is:

1. An anti-tumor agent comprising an effective amount of attenuated *Salmonella typhimurium* containing a plasmid carrying a coding sequence encoding a truncated human interleukin-2, wherein the coding sequence encoding the truncated human interleukin-2 consists of SEQ ID NO: 1.

* * * * *